United States Patent [19]

Trinh et al.

[11] Patent Number: 5,833,999
[45] Date of Patent: *Nov. 10, 1998

[54] PERSONAL TREATMENT COMPOSITIONS AND /OR COSMETIC COMPOSITIONS CONTAINING ENDURING PERFUME

[75] Inventors: Toan Trinh, Maineville; Dennis Ray Bacon, Milford; Angie Trandai, West Chester, all of Ohio

[73] Assignee: The Proctor & Gamble Company, Cincinnati, Ohio

[ * ] Notice: The term of this patent shall not extend beyond the expiration date of Pat. No. 5,540,853.

[21] Appl. No.: 745,385

[22] Filed: May 20, 1996

Related U.S. Application Data

[63] Continuation of Ser. No. 326,620, Oct. 20, 1994, abandoned.

[51] Int. Cl.$^6$ ........................................................ A61K 7/48
[52] U.S. Cl. .............................. 424/401; 424/59; 424/60; 424/65; 424/70.1; 510/101; 514/844; 514/845; 514/846; 514/944
[58] Field of Search .................................... 424/401, 70.1, 424/65, 59, 60; 514/844–846, 944; 510/101

[56] References Cited

U.S. PATENT DOCUMENTS

| | | | |
|---|---|---|---|
| 4,944,937 | 7/1990 | McCall | 424/65 |
| 4,985,238 | 1/1991 | Tanner et al. | 424/66 |
| 5,019,375 | 5/1991 | Tanner et al. | 424/66 |
| 5,069,897 | 12/1991 | Orr | 424/66 |
| 5,073,372 | 12/1991 | Turner et al. | 424/401 |
| 5,156,834 | 10/1992 | Beckmeyer et al. | 424/47 |
| 5,169,626 | 12/1992 | Tanner et al. | 424/66 |
| 5,200,174 | 4/1993 | Gardlik et al. | 424/66 |
| 5,284,649 | 2/1994 | Juneja | 424/67 |
| 5,298,236 | 3/1994 | Orr et al. | 424/47 |
| 5,318,774 | 6/1994 | Alban et al. | 424/59 |
| 5,482,635 | 1/1996 | Behan et al. | 252/8.6 |
| 5,540,383 | 7/1996 | Trinh et al. | 510/101 |

OTHER PUBLICATIONS

"A Quantitative Study of Factors that Influence the Substantivity of Fragrance Chemicals on Laundered and Dried Fabrics", Escher et al., JAOCS, vol. 71, No. 1 (Jan. 1994).
"What Makes a Fragrance Substantive?", Muller et al., Givaudan–Roure Research Ltd., CH–6800 Dubendorf Switzerland (Oct. 1992).

*Primary Examiner*—Jyothsna Venkat
*Attorney, Agent, or Firm*—Robert B. Aylor

[57] ABSTRACT

Personal treatment compositions including leave-on hair care compositions and leave-on skin care compositions, comprising from about 0.001% to about 50%, preferably from about 0.005% to about 6%, enduring perfume, are disclosed. The enduring perfume provides a lasting olfactory sensation thus minimizing the need to use large amounts.

12 Claims, No Drawings

5,833,999

PERSONAL TREATMENT COMPOSITIONS AND /OR COSMETIC COMPOSITIONS CONTAINING ENDURING PERFUME

This is a continuation of application Ser. No. 08/326,620, filed on Oct. 20, 1994 now abandoned.

TECHNICAL FIELD

The present invention relates to personal cleansing and/or cosmetic compositions containing enduring perfumes which are less likely to irritate skin and which provide efficient and long lasting perfume benefit, even after rinsing.

BACKGROUND OF THE INVENTION

Perfume in personal cleansing and cosmetic products provides olfactory aesthetic benefit and/or serves as a signal of cleanliness. These are especially important functions of these personal care products. Personal care products generally include "rinse-off" products, such as soaps, liquid soaps, shampoos, hair conditioners, etc., which are applied to, e.g., skin or hair and then rinsed off from the skin or hair, and "leave-on" products, such as skin moisturizers, sun screen products, deodorants, hair sprays, mousse, etc., which are applied and are normally allowed to remain on, e.g., skin or hair.

Continuous efforts are made to find improvements in both perfume delivery effectiveness and longevity on the body (e.g., skin and hair). During a cleansing process, a substantial amount of perfume in the personal cleanser compositions is lost with the rinse water and in the subsequent drying. On the other hand, some products, especially leave-on and cosmetic products can leave a considerable amount of material, including perfume material, on the body. It is extremely important that any material left on the body provide the maximum effect with the minimum amount of material, and that the material be as safe and non-irritating as possible.

People skilled in the perfume art, usually by experience, have some knowledge of some particular perfume ingredients that are "substantive" and/or non-irritating. Substantive perfume ingredients are those odorous compounds that effectively deposit on skin or hair in the cleaning process and are detectable on the subsequently dried skin or hair by people with normal olfactory acuity. The knowledge of what perfume ingredients are substantive is spotty and incomplete.

The object of this invention is to provide personal cleansing compositions containing enduring perfumes which are effectively retained and remain on the skin or hair for a long lasting aesthetic benefit with minimum amount of material, and not lost and/or wasted in the cleaning and drying steps. It is also an object to provide perfumes that are non-irritating insofar as that is possible.

SUMMARY OF THE INVENTION

The present invention relates to personal treatment compositions comprising perfumes that provide a long lasting aesthetic benefit with a minimum amount of material ("enduring perfume") and which are relatively non-irritating. The present invention, in one aspect, especially relates to cleansing compositions that are normally rinsed, preferably comprising, by weight of the composition:

(A) from about 0.001% to about 10%, preferably from about 0.005% to about 6%, more preferably from about 0.01% to about 4%, by weight of an enduring perfume composition;

(B) from about 0.01% to about 95%, preferably from about 5% to about 85%, more preferably from about 3% to about 30%, even more preferably from about 5% to about 22%, of a surfactant system; and (C) the balance comprising carrier, normally liquid, including water, $C_1$–$C_4$ monohydric alcohols, $C_2$–$C_6$ polyhydric alcohols, propylene carbonate, liquid polyalkylene glycols, and the like, and mixtures thereof, wherein the pH is from about 4 to about 11, preferably from about 4.5 to about 10.5, more preferably from about 5 to about 10.

Some of these cleansing compositions are meant to be used and then rinsed off. The enduring perfume compositions are desirable for such personal cleansing compositions that are intended to be rinsed off, since the enduring perfume compositions deposit extremely efficiently. In another aspect, enduring perfume compositions are used in other personal treatment compositions, including cosmetics, skin treatment compositions, and/or cleansing compositions that are meant to be left on the skin, or simply wiped off, thereby leaving a substantial amount of material on the skin. The enduring perfume compositions are extremely desirable for such personal treatment compositions since they require minimal material to provide long lasting effects even when the skin is in contact with the water, as when swimming. Personal treatment compositions such as deodorants, perfumes, colognes, suntan lotions, skin softening lotions, etc., which are meant to leave relatively large amounts of material on the skin, are especially improved by use of these enduring perfume compositions, since they minimize the amount of material in contact with the skin.

DETAILED DESCRIPTION OF THE INVENTION

The present invention relates to personal treatment compositions, including personal cleansing compositions comprising, by weight of the personal cleansing composition:

(A) from about 0.001% to about 10%, preferably from about 0.005% to about 6%, more preferably from about 0.01% to about 4%, even more preferably from about 0.01 to about 1% by weight of an enduring perfume composition;

(B) from about 0.01% to about 95%, preferably from about 5% to about 85%, more preferably from about 3% to about 30%, even more preferably from about 5% to about 22%, of a surfactant system; and (C) the balance comprising liquid carrier, normally comprising material selected from the group consisting of: water; $C_1$–$C_4$ monohydric alcohols; $C_2$–$C_6$ polyhydric alcohols; propylene carbonate; liquid polyalkylene glycols; and the like; and mixtures thereof, wherein the pH is from about 4 to about 11, preferably from about 4.5 to about 10.5, more preferably from about 5 to about 10, said enduring perfume composition preferably having at least about 70%, more preferably at least about 75%, even more preferably at least about 80%, and yet more preferably more than about 85%, of components with a ClogP$\geq$3.0 and a boiling point of $\geq$250° C.

The present invention also relates in one aspect to personal treatment compositions, e.g., those selected from the group consisting of: deodorants; antiperspirants; skin lotions; suntan lotions; perfumes, and colognes, all of which are normally applied to one, or more, parts of the body and incompletely removed, said personal treatment compositions containing an effective amount of said enduring perfume compositions.

A. Enduring Perfume Composition

Personal treatment, e.g., cleansing and/or cosmetic compositions in the art commonly contain perfumes to provide a good odor to the body. These conventional perfume compositions are normally selected mainly for their odor quality, with some consideration of substantivity.

Enduring perfume ingredients, as disclosed herein, can be formulated into personal cleansing and/or cosmetic compositions, including liquid personal cleansing compositions, and are substantially deposited and remain on the body throughout any rinse and/or drying steps. These enduring perfume ingredients minimize the material wasted, while still providing the good aesthetics that the consumers value.

An enduring perfume ingredient is characterized by its boiling point (B.P.) and its octanol/water partitioning coefficient (P). The octanol/water partitioning coefficient of a perfume ingredient is the ratio between its equilibrium concentrations in octanol and in water. The perfume ingredients of this invention have a B.P., measured at the normal, standard pressure, of about 250° C. or higher, preferably more than about 260° C.; and an octanol/water partitioning coefficent P of about 1,000 or higher. Since the partitioning coefficients of the perfume ingredients of this invention have high values, they are more conveniently given in the form of their logarithm to the base 10, logP. Thus the perfume ingredients of this invention have logP of about 3 or higher, preferably more than about 3.1, and even more preferably more than about 3.2.

The boiling points of many perfume ingredients are given in, e.g., "Perfume and Flavor Chemicals (Aroma Chemicals)," Steffen Arctander, published by the author, 1969, incorporated herein by reference.

The logP of many perfume ingredients has been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are preferably used instead of the experimental logP values in the selection of perfume ingredients which are useful in the present invention.

Thus, when a perfume composition which is composed of ingredients having a B.P. of about 250° C. or higher and a ClogP of about 3 or higher, is used in a liquid personal cleansing composition, the perfume is very effectively deposited on skin or hair, and remains substantive after the rinsing and drying steps. Also, surprisingly, these same perfume compositions are very mild to skin and are relatively non-irritating, even on leave-on products.

Table 1 gives some non-limiting examples of enduring perfume ingredients, useful in liquid personal cleansing compositions of the present invention. The enduring perfume compositions of the present invention contain at least about 3 different enduring perfume ingredients, more preferably at least about 4 different enduring perfume ingredients, and even more preferably at least about 5 different enduring perfume ingredients. Furthermore, the enduring perfume compositions of the present invention contain at least about 60 wt. % of enduring perfume ingredients, preferably at least about 70 wt. % of enduring perfume ingredients, more preferably at least about 80 wt. % of enduring perfume ingredients, and even more preferably at least about 85 wt. % of enduring perfume ingredients. Personal cleansing compositions of the present invention contain from about 0.001% to about 10%, preferably from about 0.005% to about 6%, more preferably from about 0.01% to about 4%, and even more preferably from about 0.01% to about 1%, of an enduring perfume composition. Hair care and topical skin care compositions that are not normally rinsed off can contain from 0.001% to about 50%, preferably from about 0.001% to about 15%, more preferably from about 0.005% to about 6%, most preferably from about 0.01% to about 4%, and yet more preferably from about 0.01% to about 1%, of said enduring perfume compositions. The high levels are associated mainly with body perfumes, such as fine fragrances, eau de toilette, eau de cologne, etc.

In the perfume art, some materials having no odor or very faint odor are used as diluents or extenders. Non-limiting examples of these materials are dipropylene glycol, diethyl phthalate, triethyl citrate, isopropyl myristate, and benzyl benzoate. These materials are used for, e.g., solubilizing or diluting some solid or viscous perfume ingredients to, e.g., improve handling and/or formulating, or stabilizing volatile ingredients, e.g., by reducing their vapor pressure. These materials are not counted in the definition/formulation of the enduring perfume compositions of the present invention.

Non-enduring perfume ingredients, which are preferably minimized in personal treatment, e.g., liquid personal cleansing compositions of the present invention, are those having a B.P. of less than about 250° C., or having a ClogP of less than about 3.0, or having both a B.P. of less than about 250° C. and a ClogP of less than about 3.0. Table 2 gives some non-limiting examples of non-enduring perfume ingredients. In some particular fabric softener compositions, some non-enduring perfume ingredients can be used in small amounts, e.g., to improve product odor. However, to minimize waste, the enduring perfume compositions of the present invention contain less than about 30 wt. % of non-enduring perfume ingredients, preferably less than about 25 wt. % of non-enduring perfume ingredients, more preferably less than about 20 wt. % of non-enduring perfume ingredients, and even more preferably less than about 15 wt. % of non-enduring perfume ingredients.

TABLE 1

Examples of Enduring Perfume Ingredients

| Perfume Ingredients<br>BP > 250° C. and ClogP > 3.0 | Approximate<br>B.P. (°C.) (a) | ClogP |
|---|---|---|
| Allyl cyclohexane propionate | 267 | 3.935 |
| Ambrettolide | 300 | 6.261 |
| Amyl benzoate | 262 | 3.417 |
| Amyl cinnamate | 310 | 3.771 |
| Amyl cinnamic aldehyde | 285 | 4.324 |
| Amyl cinnamic aldehyde dimethyl acetal | 300 | 4.033 |
| iso-Amyl salicylate | 277 | 4.601 |
| Aurantiol | 450 | 4.216 |
| Benzophenone | 306 | 3.120 |

TABLE 1-continued

Examples of Enduring Perfume Ingredients

| Perfume Ingredients<br>BP > 250° C. and ClogP > 3.0 | Approximate<br>B.P. (°C.) (a) | ClogP |
|---|---|---|
| Benzyl salicylate | 300 | 4.383 |
| para-tert-Butyl cyclohexyl acetate | +250 | 4.019 |
| iso-Butyl quinoline | 252 | 4.193 |
| beta-Caryophyllene | 256 | 6.333 |
| Cadinene | 275 | 7.346 |
| Cedrol | 291 | 4.530 |
| Cedryl acetate | 303 | 5.436 |
| Cedryl formate | +250 | 5.070 |
| Cinnamyl cinnamate | 370 | 5.480 |
| Cyclohexyl salicylate | 304 | 5.265 |
| Cyclamen aldehyde | 270 | 3.680 |
| Dihydro isojasmonate | +300 | 3.009 |
| Diphenyl methane | 262 | 4.059 |
| Diphenyl oxide | 252 | 4.240 |
| Dodecalactone | 258 | 4.359 |
| iso E super | +250 | 3.455 |
| Ethylene brassylate | 332 | 4.554 |
| Ethyl methyl phenyl glycidate | 260 | 3.165 |
| Ethyl undecylenate | 264 | 4.888 |
| Exaltolide | 280 | 5.346 |
| Galaxolide | +250 | 5.482 |
| Geranyl anthranilate | 312 | 4.216 |
| Geranyl phenyl acetate | +250 | 5.233 |
| Hexadecanolide | 294 | 6.805 |
| Hexenyl salicylate | 271 | 4.716 |
| Hexyl cinnamic aldehyde | 305 | 5.473 |
| Hexyl salicylate | 290 | 5.260 |
| alpha-Irone | 250 | 3.820 |
| Lilial (p-t-bucinal) | 258 | 3.858 |
| Linalyl benzoate | 263 | 5.233 |
| 2-Methoxy naphthalene | 274 | 3.235 |
| Methyl dihydrojasmone | +300 | 4.843 |
| gamma-n-Methyl ionone | 252 | 4.309 |
| Musk indanone | +250 | 5.458 |
| Musk ketone | MP = 137° C. | 3.014 |
| Musk tibetine | MP = 136° C. | 3.831 |
| Myristicin | 276 | 3.200 |
| Oxahexadecanolide-10 | +300 | 4.336 |
| Oxahexadecanolide-11 | MP = 35° C. | 4.336 |
| Patchouli alcohol | 285 | 4.530 |
| Phantolide | 288 | 5.977 |
| Phenyl ethyl benzoate | 300 | 4.058 |
| Phenylethylphenylacetate | 325 | 3.767 |
| Phenyl heptanol | 261 | 3.478 |
| Phenyl hexanol | 258 | 3.299 |
| alpha-Santalol | 301 | 3.800 |
| Thibetolide | 280 | 6.246 |
| delta-Undecalactone | 290 | 3.830 |
| gamma-Undecalactone | 297 | 4.140 |
| Vetiveryl acetate | 285 | 4.882 |
| Yara-yara | 274 | 3.235 |
| Ylangene | 250 | 6.268 |

(a) M.P. is melting point; these ingredients have a B.P. higher than 250° C.

TABLE 2

Examples of Non-Enduring Perfume Ingredients

| Perfume Ingredients | Approximate<br>B.P. (°C.) | ClogP |
|---|---|---|
| BP < 250° C. and ClogP < 3.0 | | |
| Benzaldehyde | 179 | 1.480 |
| Benzyl acetate | 215 | 1.960 |
| laevo-Carvone | 231 | 2.083 |
| Geraniol | 230 | 2.649 |
| Hydroxycitronellal | 241 | 1.541 |
| cis-Jasmone | 248 | 2.712 |
| Linalool | 198 | 2.429 |

TABLE 2-continued

Examples of Non-Enduring Perfume Ingredients

| Perfume Ingredients | Approximate<br>B.P. (°C.) | ClogP |
|---|---|---|
| Nerol | 227 | 2.649 |
| Phenyl ethyl alcohol | 220 | 1.183 |
| alpha-Terpineol | 219 | 2.569 |
| BP > 250° C. and ClogP < 3.0 | | |
| Coumarin | 291 | 1.412 |
| Eugenol | 253 | 2.307 |
| iso-Eugenol | 266 | 2.547 |
| Indole | 254<br>decompos | 2.142 |
| Methyl cinnamate | 263 | 2.620 |
| Methyl dihydrojasmonate | +300 | 2.275 |
| Methyl-N-methyl anthranilate | 256 | 2.791 |
| beta-Methyl naphthyl ketone | 300 | 2.275 |
| delta-Nonalactone | 280 | 2.760 |
| Vanillin | 285 | 1.580 |
| BP < 250° C. and ClogP > 3.0 | | |
| iso-Bornyl acetate | 227 | 3.485 |
| Carvacrol | 238 | 3.401 |
| alpha-Citronellol | 225 | 3.193 |
| para-Cymene | 179 | 4.068 |
| Dihydro myrcenol | 208 | 3.030 |
| Geranyl acetate | 245 | 3.715 |
| d-Limonene | 177 | 4.232 |
| Linalyl acetate | 220 | 3.500 |
| Vertenex | 232 | 4.060 |

B. Personal Cleansing Compositions Which Are Normally Rinsed Off

I. Surfactant System

Some preferred surfactants for use in the surfactant systems herein, as well as other cleansing product ingredients, are disclosed in the following references:

| Pat. No. | Issue Date | Inventor(s) |
|---|---|---|
| 4,061,602 | 12/1977 | Oberstar et al |
| 4,234,464 | 11/1980 | Morshauser |
| 4,472,297 | 9/1984 | Bolich et al. |
| 4,491,539 | 1/1985 | Hoskins et al. |
| 4,540,507 | 9/1985 | Grollier |
| 4,565,647 | 1/1986 | Llenado |
| 4,673,525 | 6/1987 | Small et al. |
| 4,704,224 | 11/1987 | Saud |
| 4,788,006 | 11/1988 | Bolich, Jr., et al. |
| 4,812,253 | 3/1989 | Small et al. |
| 4,820,447 | 4/1989 | Medcalf et al. |
| 4,906,459 | 3/1990 | Cobb et al. |
| 4,923,635 | 5/1990 | Simion et al. |
| 4,954,282 | 9/1990 | Rys et al. |

All of said patents are incorporated herein by reference.

Numerous examples of other surfactants are disclosed in the patents incorporated herein by reference. They include anionic surfactants, nonionic surfactants, cationic surfactants, amphoteric surfactants, zwitterionic surfactants, and mixtures thereof. They include alkyl sulfates, alkylpolyethyleneglycol sulfates, alkyl sulfonates, alkyl glyceryl ether sulfonates, anionic acyl sarcosinates, methyl acyl laurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the alkylpolyethyleneglycol sulfate surfactants are the alkyl ether sulfates with 1 to 12 ethoxy groups, especially ammonium and sodium lauryl ether sulfates.

The hydrophobic, e.g., alkyl, chains for the surfactants are normally $C_8$–$C_{22}$, preferably $C_{10}$–$C_{18}$.

1. Anionic Detergent Surfactants a. Soap

Some preferred compositions of the present invention contain soaps derived from essentially saturated hydrocarbon chainlengths of from about 8 to about 22 carbon atoms. It is preferred that the soap be the sodium and/or potassium salts, but other soluble soaps can be used.

b. Synthetic Anionic Detergent Surfactants

Anionic nonsoap synthetic detergent surfactants can be exemplified by the alkali metal salts of organic sulfuric reaction products having in their molecular structure an alkyl radical containing from 8 to 22 carbon atoms and a sulfonic acid or sulfuric acid ester radical (included in the term alkyl is the alkyl portion of higher acyl radicals).

c. Sulfate Surfactants

The compositions hereof can comprise alkyl sulfate, alkyl ether sulfate, fatty acid monoglyceride sulfate, or mixtures thereof, as a surfactant component. Typically, such sulfate surfactants, when present, are at a level of from about 1% to about 30%, preferably from about 10% to about 25%, more preferably from about 12% to about 22%, most preferably from about 15% to about 22%, by weight of the composition. These materials have the respective formulae (I) $ROSO_3M$ and (II) $RO(C_2H_4O)_xSO_3M$, wherein R is alkyl or alkenyl of from about 8 to about 30 carbon atoms, x is 1 to 10, and M is H or a soluble salt-forming cation such as ammonium, alkanolammonium (such as triethanolammonium), monovalent metal cations, such as sodium and/or potassium, polyvalent metal cations, such as magnesium and calcium, and/or mixtures of such cations. The cation M, of the anionic surfactant should be chosen such that the anionic surfactant component is water soluble. Solubility will depend upon the particular anionic surfactants and/or cations chosen. As an aid to determining appropriate mixtures of anionic surfactants, the anionic surfactants should be chosen such that the Krafft temperature of the surfactants is about 15° C. or less, preferably about 10° C. or less, more preferably about 0° C. or less. It is also preferred that the anionic surfactant be soluble in the composition hereof.

Preferably, R has from about 10 to about 18 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil, palm kernel oil, or tallow, or can be synthetic. Such alcohols are preferably reacted with about 1 to about 10, more preferably from about 1 to about 4, most preferably from about 2 to about 3.5, molar proportions of ethylene oxide and the resulting mixture of molecular species having, for example, an average of 3 moles of ethylene oxide per mole of alcohol, is sulfated and neutralized.

Specific examples of alkyl ether sulfates which can be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide.

d. Sulfonate Detergent Surfactants

A suitable class of optional anionic detersive surfactants are aliphatic sulfonates such as represented by the water-soluble salts of the organic, sulfuric acid reaction products of the general formula (I):

$$R_1\text{—}SO_3\text{—}M \qquad (I)$$

wherein $R_1$ is chosen from the group consisting of a straight or branched chain, saturated aliphatic hydrocarbon radical having from about 8 to about 24, preferably about 12 to about 18, carbon atoms; and M is a cation, as previously described, subject to the same limitations regarding polyvalent metal cations as previously discussed. Important examples are the salts of an organic sulfuric acid reaction product of a hydrocarbon of the methane series, including iso-, neo-, and n-paraffins, having about 8 to about 24 carbon atoms, preferably about 12 about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12}$–$C_{18}$ paraffins (e.g., normal and secondary paraffins).

Additional examples of synthetic anionic sulfonate detersive surfactants which can be added to the compositions of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil, and fatty acid monoglyceride sulfonates as described in the patents incorporated herein by reference.

Still other synthetic anionic detersive surfactants are in the class designated as succinates. This class includes such surface active agents as disodium N-octadecylsulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; dioctyl esters of sodium sulfosuccinic acid.

Other suitable anionic detersive surfactants include olefin sulfonates having about 12 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example, by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

Another class of anionic detersive surfactants are the beta-alkyloxy alkane sulfonates. These compounds have the following formula (II):

$$R_1C(OR_2)(H)CH_2SO_3M \qquad (II)$$

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

e. N-Acylamino Acid Surfactants

Yet other anionic detergent surfactant type is the N-acylamino acid surfactant type, which includes N-acyl hydrocarbyl acids and salts thereof, such as those represented by Formula III, as follows:

$$R^1-C(O)-N(R^2)-(R^3)_n COOM \qquad (III)$$

wherein: $R^1$ is a $C_7$–$C_{23}$ alkyl or alkenyl radical, preferably $C_9$–$C_{17}$; $R^2$ is —H, $C_1$–$C_4$ alkyl, phenyl, or —CH$_2$COOM, preferably $C_1$–$C_4$ alkyl, more preferably $C_1$–$C_2$ alkyl; $R^3$ is —CR$^4_2$— or $C_1$–$C_2$ alkoxy, wherein each $R^4$ independently is —H or $C_1$–$C_6$ alkyl or alkylester, and n is from 1 to 4, preferably 1 or 2; and M is —H or a cation as previously defined, preferably an alkali metal such as sodium or potassium.

A wide variety of N-acyl acid surfactants and their synthesis are described in Anionic Surfactants, Part II, Surfactant Science Series, Vol. VII, edited by Warner M. Linfield, Marcel Dekker, Inc. (New York and Basel), 1976; pp 581–617.

Especially preferred are compounds of Formula III wherein $R^2$ is methyl and $R^3$ is —CH$_2$—, and n is 1, which are known as the N-acyl sarcosinates, and acids thereof. Specific examples include lauroyl sarcosinate, myristoyl sarcosinate, cocoyl sarcosinate, and oleoyl sarcosinate, preferably in their sodium and potassium salt forms.

Preferred anionic detersive surfactants for use in the present compositions include the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water-soluble salts of condensation products of fatty acids with sarcosine; and others known in the art.

Some examples of good lather-enhancing, mild anionic detergent surfactants are e.g., sodium or potassium lauroyl sarcosinate, alkyl glyceryl ether sulfonate, sulfonated fatty esters, and sulfonated fatty acids.

Other synthetic detergent surfactants which can be used include amphoteric, zwitterionic, nonionic and, in certain instances, cationic surfactants, e.g., at a level of from about 1% to about 10%, preferably from about 2% to about 6% by weight of the product.

2. Amphoteric Detergent Surfactants

Examples of amphoteric surfactants which can be used in the compositions of the present invention are those which are broadly described as derivatives of aliphatic secondary, tertiary, and/or quaternary amines in which at least one hydrophobic, e.g., aliphatic, radical which can be either straight or branched chain and which typically contains from about 8 to about 18 carbon atoms and in which at least one radical contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438, 091, and the products sold under the trade name "Miranol" and described in U.S. Pat. No. 2,528,378.

The amphoteric surfactants hereof also include the imidazolinium amphoteric (zwitterionic) surfactants such as those depicted by Formula (IV):

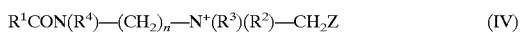

$$R^1CON(R^4)-(CH_2)_n-N^+(R^3)(R^2)-CH_2Z \qquad (IV)$$

wherein $R^1$ is $C_8$–$C_{22}$ alkyl or alkenyl, preferably $C_{12}$–$C_{16}$, $R^2$ is hydrogen or CH$_2$CO$_2$M, $R^3$ is CH$_2$CH$_2$OH or CH$_2$CH$_2$OCH$_2$CH COOM, $R^4$ is hydrogen, CH$_2$CH$_2$OH, or CH$_2$CH$_2$OCH$_2$CH$_2$COOM, Z is CO$_2$M or CH$_2$CO$_2$M, n is 2 or 3, preferably 2, M is hydrogen or a cation, such as alkali metal, alkaline earth metal, ammonium, or alkanol ammonium.

Suitable materials of this type are marketed under the tradename Miranol® and are understood to comprise a complex mixture of species, and can exist in protonated and non-protonated species depending upon pH with respect to species that can have a hydrogen at $R^2$. The imidazolinum amphoteric surfactant hereof can be derived via an imidazolinium intermediate. However, it will be recognized by those in the art that it needn't necessarily be derived via an imidazolinium.

Preferred amphoteric surfactants of Formula IV are monocarboxylates and dicarboxylates. Examples of these materials include cocoamphocarboxy-propionate, cocoamphocarboxypropionic acid, cocoamphocarboxyglycinate (alternately referred to as cocoamphodiacetate), and cocoamphoacetate.

Specific commercial products providing the imidazolinium derivative component of the present compositions include those sold under the trade names Miranol C2M CONC. N.P., Miranol C2M CONC. O.P., Miranol C2M SF, Miranol CM Special (Miranol, Inc.); Alkateric® 2CIP (Alkaril Chemicals); Amphoterge® W-2 (Lonza, Inc.); Monateric® CDX-38, Monateric CSH-32 (Mona Industries); Rewoteric® AM-2C (Rewo Chemical Group); and Scheroteric® MS-2 (Scher Chemicals).

Amphoteric surfactants also include aminoalkanoates of the formula (V):

$$R-NH(CH_2)_n COOM; \qquad (V)$$

and iminodialkanoates of the formula (VI):

$$R-N[(CH_2)_m COOM]_2 \qquad (VI)$$

and mixtures thereof, wherein n and m are numbers from 1 to 4, R is $C_8$–$C_{22}$ alkyl or alkenyl, and M is hydrogen, alkali metal, alkaline earth metal, ammonium or alkanolammonium.

Examples of such amphoteric surfactants include n-alkylaminopropionates and n-alkyliminodipropionates. Such materials are sold under the tradename Deriphat® by Henkel and Mirataine® by Miranol, Inc. Specific examples include N-lauryl-beta-amino propionic acid or salts thereof, and N-lauryl-beta-imino-dipropionic acid or salts thereof.

Other zwitterionic surfactants, in addition to the imidazoliniums, can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula (VII) for these compounds is:

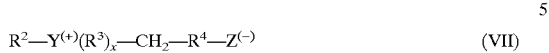

$$R^2—Y^{(+)}(R^3)_x—CH_2—R^4—Z^{(-)} \qquad \text{(VII)}$$

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; x is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-P-diethyl-P-3,6,9-trioxatetradexocylphosphonio]-2-hydroxypropane-1-phosphate; 3-[N,N-dipropyl-N-3-dodecoxy-2-hydroxypropylammonio]-propane1-phosphonate; 3-(N,N-dimethyl-N-hexadecylammonio)propane-1-sulfonate; 3-(N,N-dimethyl-N-hexadecylammonio)-2-hydroxypropane-1-sulfonate; 4-[N,N-di(2-hydroxyethyl)-N-(2-hydroxydodecyl)ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Zwitterionic detergent surfactants containing an amido linkage in the hydrophobic chain are especially desirable and include those represented by the Formula (VIII):

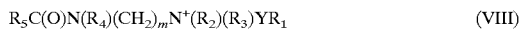

$$R_5C(O)N(R_4)(CH_2)_mN^+(R_2)(R_3)YR_1 \qquad \text{(VIII)}$$

wherein: $R_1$ is a member selected from the group consisting of: COOM and CH(OH)— $CH_2SO_3M$; $R_2$ is $C_1$–$C_3$ alkyl or hydroxy ($C_1$–$C_3$) alkyl; $R_3$ is $C_1$–$C_3$ alkyl or hydroxy ($C_1$–$C_3$) alkyl; $R_4$ is a member selected from the group consisting of hydrogen and $C_1$–$C_3$ alkyl; $R_5$ is $C_8$–$C_{20}$ alkyl or alkenyl; Y is $C_1$–$C_3$ alkyl; m is an integer from 2 to 7; n is the integer 1 or 0; M is hydrogen or a cation, such as an alkali metal or alkaline earth cation metal, ammonium, or alkanolamide.

The term "alkyl" or "hydroxyalkyl" means straight or branch chained, saturated, aliphatic hydrocarbon radicals and substituted hydrocarbon radicals such as, for example, methyl, ethyl, propyl, isopropyl, hydroxypropyl, hydroxyethyl, and the like.

Examples of zwitterionics useful herein include the higher alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis(2-hydroxyethyl)carboxy methyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, etc. The sulfobetaines can be represented by coco dimethyl sulfopropyl betaine, stearyl dimethyl sulfopropyl betaine, lauryl bis-(2-hydroxyethyl) sulfopropyl betaine, amido betaine, amido sulfobetaines, and the like.

3. Cationic Detergent Surfactants

Many cationic surfactants are known to the art. By way of example, the following can be mentioned:
stearyldimethylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride;
laurylpyridinium chloride;
laurylisoquinolium bromide;
ditallow(hydrogenated)dimethyl ammonium chloride;
dilauryldimethyl ammonium chloride; and
stearalkonium chloride.

4. Nonionic Detergent Surfactants

Nonionic surfactants are typically compounds produced by the condensation of alkylene oxide groups (hydrophilic in nature) with an organic hydrophobic compound, which can be aliphatic or alkyl aromatic in nature, but can include other surfactants that do not possess a charge group. Examples of preferred classes of nonionic surfactants are:

a. Alkyl phenol ethoxylates. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds can be derived from polymerized propylene, diisobutylene, octane, or nonane, for example.

b. Polyethylene glycol/polypropylene glycol block copolymers. Those derived from the condensation of ethylene oxide with the product resulting from the reaction of propylene oxide and ethylene diamine products which can be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

c. Fatty alcohol and fatty acid ethoxylates. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

d. Long chain tertiary amine oxides. Long chain tertiary amine oxides corresponding to the following general formula:

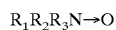

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxy ethyl) amine oxide, dimethyloctylamine oxide, dimethyldecylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethyl-hexadecylamine oxide.

e. Long chain tertiary phosphine oxides. Long chain tertiary phosphine oxides corresponding to the following general formula:

RR'R"P→O wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyldi(2-hydroxyethyl)phosphine oxide, tetra-decylmethyl-2-hydroxypropylphosphine oxide, oleyldimethylphosphine oxide, 2-hydroxydodecyldimethylphosphine oxide.

f. Long chain dialkyl sulfoxides. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecyl methyl sulfoxide, 3-hydroxytridecyl methyl sulfoxide, 3-hydroxy-4-dodecoxybutyl methyl sulfoxide.

g. Alkyl polysaccharide (APS) surfactants such as the alkyl polyglycosides. Such surfactants are APS surfactants having a hydrophobic group with about 6 to about 30 carbon atoms and polysaccharide (e.g., polyglycoside) as the hydrophilic group. Optionally, there can be a polyalkylene-oxide group joining the hydrophobic and hydrophilic moieties. The alkyl group (i.e., the hydrophobic moiety) can be saturated or unsaturated, branched or unbranched, and unsubstituted or substituted (e.g., with hydroxy or cyclic rings).

h. Polyethylene glycol (PEG) glyceryl fatty esters, such as those of the formula R(O)OCH$_2$CH(OH)CH$_2$(OCH$_2$CH$_2$)$_n$OH wherein n is from about 5 to about 200, preferably from about 20 to about 100, and R is an aliphatic hydrocarbyl having from about 8 to about 20 carbon atoms.

Many additional nonsoap surfactants are described in McCutcheon's, Detergents And Emulsifiers, 1994 Annual, published by MC Publishing Company, which is incorporated here by reference, and in U.S. Pat. No. 5,151,209, to McCall et al., issued Sep. 29, 1992; U.S. Pat. No. 5,151,210, to Steuri et al., issued Sep. 29, 1992; and U.S. Pat. No. 5,120,532, to Wells et al., issued Jun. 9, 1992, all of which are incorporated by reference herein. For the purposes of the surfactants described herein, it should be understood that the terms "alkyl" or "alkenyl" include mixtures of radicals which can contain one or more intermediate linkages such as ether or polyether linkages or non-functional substituents such as hydroxyl or halogen radicals wherein the radical remains of hydrophobic character.

5. The Surfactant Systems

The present invention, especially in the aspect relating to personal cleansing compositions that are normally rinsed, like shampoos and personal skin cleansers, comprises from about 0.01% to about 95%, preferably from about 5% to about 85%, more preferably from about 3% to about 30%, even more preferably from about 5% to about 22% of a surfactant system. This surfactant system comprises anionic, nonionic, cationic, and/or zwitterionic type surfactants as described hereinbefore. For non-shampoo surfactant systems the surfactant system typically comprises at least one surfactant selected from the group consisting of soap, acylglutamates, alkyl sarcosinates, alkylpolyethyleneglycol sulfates, alkylglyceryl ether sulfonates, and/or acyl isethionates.

a. Shampoo Surfactant Systems

The shampoo compositions of the present invention typically contain a detersive surfactant system to provide cleaning performance to the composition. The total detersive surfactant component will generally be present at a level from about 1% to about 30%, by weight of the composition, preferably from about 12% to about 25%, more preferably from about 15% to about 22%.

The shampoo compositions of the present invention optionally comprise from 0% to about 20% of surfactants that build suds. When used, such optional suds building surfactants are typically present at levels of from about 0.05% to about 20%, more typically from about 0.1% to about 10%, preferably from about 0.5% to about 5%, although higher or lower levels can be used. Suitable surfactants for building suds include amide foam boosters, e.g., fatty acid (e.g., $C_{10}$–$C_{22}$) mono- and di-($C_1$–$C_5$, especially $C_1$–$C_3$) alkanol amides at a level of from about 0.1% to about 6%, preferably from about 0.5% to about 4%.

b. Soap Surfactant Systems

Compositions of the present invention can comprise at least about 2% by weight of the surfactant system, preferably at least about 10%, more preferably at least about 25%, and even more preferably at least about 50% soap.

Preferably the alkali metal soap is $C_{10}$–$C_{22}$, preferably $C_{12}$–$C_{18}$, more preferably $C_{12}$–$C_{14}$ (cocoate, laurate, PKO) sodium, potassium, ammonium, triethanolammonium, and/or magnesium soap. Preferably these soaps have saturated alkyl chains.

These soaps are preferably prepared by the in situ saponification of the corresponding fatty acids, but they can also be introduced as preformed soaps.

The addition of $C_{10}$–$C_{22}$ soap also decreases any "slippery feel" caused by any synthetic surfactant that is present.

A soap based liquid composition comprises:

(A) from about 5% to about 20% by weight of potassium $C_8$–$C_{22}$ fatty acid soap;

(B) from about 0.1 to about 7% $C_8$–$C_{22}$ free fatty acid;

(C) from about 8% to about 35% of a polyol selected from the group consisting of: glycerin, glycerol, propylene glycol, polypropylene glycol, polyethylene glycol, ethyl hexanediol, hexylene glycol, and other aliphatic alcohols; and mixtures thereof;

(D) from about 0.5% to about 15% petrolatum preferably having an average particle size of from 45 microns to about 120 microns; and (E) from about 0.5 to about 5% glycol ester selected from the group consisting of glycol monoesters and diesters of fatty acids with a chainlength from about 10 to about 22, and mixtures thereof, typically formulated as a liquid which additionally comprises from about 35% to about 70% water, wherein the ratio of said soap plus any synthetic surfactant, which is optionally added, to said free fatty acids plus glycol ester is preferably from about 1:1 to about 15:1 and more preferably from about 3:1 to about 12:1; wherein said liquid has a viscosity of from about 500 cps to about 60,000 cps at about 26.7° C.; and wherein the fatty acid of (A) and (B) have an Iodine Value of from zero to about 15.

The fatty acid matter of the above soap based liquid composition typically has an IV of from zero to about 15, preferably below about 10, more preferably below about 3.

The compositions can contain fatty acids derived from essentially saturated hydrocarbon chainlengths of from about 8 to about 22 carbon atoms. These fatty acids can be highly purified individual chainlengths and/or crude mixtures such as those derived from fats and oils. In general, the higher the proportion of longer chain length fatty acids, the poorer the lather, but the greater the pearlescent appearance and mildness of the product.

The above soap based liquid composition can contain from about 8% to about 35% of a polyol selected from the group consisting of: glycerin, glycerol, propylene glycol, polypropylene glycol, polyethylene glycol, ethyl hexanediol, hexylene glycol, aliphatic alcohol; and mixtures thereof, and preferably contains 10–30% of said polyol, preferably glycerol.

The petrolatum (emollient) useful in the above soap based liquid composition can be any grade of white or yellow petrolatum recognized in the art as suitable for human application. The preferred type is USP Class III with a melting point between about 122° F. and about 135° F. (about 50°–57° C.). Such a material is commercially available as Penreco Snow White Pet USP. The petrolatum of the present invention includes hydrocarbon mixtures formulated with mineral oils in combination with paraffin waxes of various melting points.

Alternatively, the above soap based liquid composition can contain from about 0.5% to about 15% of a lipophilic emollient selected from the group consisting of: esters of fatty acids; glycerin mono-, di-, and tri-esters; epidermal and sebaceous hydrocarbons such as cholesterol, cholesterol esters, squalene, squalane; silicone oils and gums; mineral oil; lanolin and lanolin derivatives; and mixtures thereof.

The petrolatum and/or emollient particle size is alternatively expressed as a particle size distribution with 10% to 80% of the particles being about 5 microns to about 120 microns within the product, preferably 20% to 80% being from about 10 to about 110 microns, more preferably 25% to 80% from about 30 to about 110 microns, more preferably from about 60 to about 100 microns.

The level of water in the above soap based liquid composition is typically from about 35% to about 70%, preferably from about 40% to about 65%.

Liquid soap cleansers normally have a viscosity of from about 1 to about 150,000 cps, preferably from about 500 cps to about 120,000 cps, more preferably from about 1,000 cps to about 45,000 cps, at about 26.7° C. (about 80° F.), Brookfield RVTDCP with a Spindle CP-41 at 1 RPM for about 3 minutes.

The liquid soap is called a dispersoid because at least some of the fatty matter, at the levels used herein, is insoluble. The above soap based liquid composition is phase stable, even after storage.

II. Optional Ingredients

1. Optional Suspending Agent

The present compositions, and especially shampoo compositions, can include a crystalline suspending agent. Other suspending agents useful for suspending emulsified oils (or other materials) and for thickening the compositions can optionally be used.

The crystalline suspending agent will be used at an effective level for suspending emulsified oils or other materials. The suspension should, in general, be stable for at least one month at ambient temperature. Longer term shelf stability such as at least three months, preferably six months, most preferably at least about twenty-four months, is preferred. In general, the compositions hereof will comprise from about 0.5% to about 10%, by weight, of a crystalline suspending agent or combination thereof. The crystalline suspending agent is preferably present in the shampoo compositions hereof at a level of about 0.5% to about 5%, more preferably about 1% to about 4%, most preferably about 1% to about 3%.

Preferred crystalline suspending agents are acyl derivatives and amine oxides, especially acyl derivatives, especially those which can be solubilized in a premix solution and then be recrystallized upon cooling. These materials will comprise long chain (e.g., $C_8$–$C_{22}$ preferably $C_{14}$–$C_{22}$, more preferably $C_{16}$–$C_{22}$) aliphatic groups, i.e., long chain acyl derivative materials and long chain amine oxides, as well as mixtures of such materials. Included are ethylene glycol long chain esters, alkanol amides of long chain fatty acids, long chain esters of long chain fatty acids, glyceryl long chain esters, long chain esters of long chain alkanolamides, and long chain alkyl dimethyl amine oxides, and mixtures thereof.

Suitable suspending agents for use herein include ethylene glycol esters of fatty acids preferably having from about 14 to about 22 carbon atoms, more preferably 16–22 carbon atoms. More preferred are the ethylene glycol stearates, both mono and distearate, but particularly the distearate containing less than about 7% of the mono stearate. Other suspending agents include alkanol amides of fatty acids, preferably having from about 16 to about 22 carbon atoms, more preferably about 16 to 18 carbon atoms. Preferred alkanol amides are stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate); glyceryl esters (e.g., glyceryl distearate) and long chain esters of long chain alkanol amides (e.g., stearamide diethanolamide distearate, stearamide monoethanolamide stearate). Ethylene glycol esters of long chain carboxylic acids, long chain amine oxides, and alkanol amides of long chain carboxylic acids, in addition to the preferred materials listed above, can be used as suspending agents.

Suspending agents also include long chain amine oxides such as alkyl ($C_{16}$–$C_{22}$) dimethyl amine oxides, e.g., stearyl dimethyl amine oxide. If the compositions contain an amine oxide or a long chain acyl derivative which is a surfactant, the suspending function could also be provided by such amine oxide or acyl derivative, provided at least a portion of them are present in crystalline form, and additional suspending agent may not be needed.

Other long chain acyl derivatives that can be used include N,N-dihydrocarbyl ($C_{12}$–$C_{22}$, preferably $C_{16}$–$C_{18}$) amido benzoic acid and soluble salts thereof (e.g., Na and K salts), particularly N,N-di($C_{16}$–$C_{18}$, and hydrogenated tallow) amido benzoic acid species of this family, which are commercially available from Stepan Company (Northfield, Ill., USA).

The crystalline suspending agent serves to assist in suspending particulate matter or emulsions of insoluble fluids, i.e., oils, in the shampoo compositions hereof, and can give pearlescence to the product.

The crystalline suspending agent can be incorporated into the shampoos hereof by solubilizing it into a solution containing water and the anionic sulfate surfactant at a temperature above the melting point of the suspending agent. The suspending agent is then recrystallized, typically by cooling the solution to a temperature sufficient to induce crystallization.

2. Optional Suspending Agent Thickeners, and Viscosity Modifiers

Optional thickeners are categorized as cationic, nonionic, or anionic and are selected to provide the desired viscosities. Suitable thickeners are listed in the Glossary and Chapters 3, 4, 12 and 13 of the *Handbook of Water-Soluble Gums and Resins*, Robert L. Davidson, McGraw-Hill Book Co., New York, N.Y., 1980, incorporated by reference herein.

Anionic thickeners include crosslinked polymers. These crosslinked polymers typically contain one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred polymers for use herein are of two general types. The first type of polymer is a crosslinked homopolymer of an acrylic acid monomer or derivative thereof (e.g., wherein the acrylic acid has substituents on the two and three carbon positions independently selected from the group consisting of $C_{1-4}$ alkyl, —CN, —COOH, and mixtures thereof). The second type of polymer is a crosslinked copolymer having a first monomer selected from the group consisting of an acrylic acid monomer or derivative thereof (as just described in the previous sentence), a short chain alcohol (i.e. a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof), and mixtures thereof; and a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Combinations of these two types of polymers are also useful herein.

In the first type of crosslinked homopolymers the monomers are preferably selected from the group consisting of acrylic acid, methacrylic acid, ethacrylic acid, and mixtures thereof, with acrylic acid being most preferred. In the second type of crosslinked copolymers the acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The short chain alcohol acrylate ester monomer or derivative thereof is preferably selected from the group consisting of $C_{1-4}$ alcohol acrylate esters, $C_{1-4}$ alcohol methacrylate esters, $C_{1-4}$ alcohol ethacrylate esters, and mixtures thereof, with the $C_{1-4}$ alcohol acrylate esters, $C_{1-4}$ alcohol methacrylate esters, and mixtures thereof, being most preferred. The long chain alcohol acrylate ester monomer is selected from $C_{8-40}$ alkyl acrylate esters, with $C_{10-30}$ alkyl acrylate esters being preferred.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaerythritol, and mixtures thereof. These polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are incorporated by reference herein. See also, CTFA International Cosmetic Ingredient Dictionary, fourth edition, 1991, pp. 12 and 80; which are also incorporated herein by reference.

Other examples of anionic commercially available homopolymers useful herein include the carbomers, which are homopolymers of acrylic acid crosslinked with allyl ethers of sucrose or pentaerytritol. The carbomers are available as the Carbopol® 900 series from B.F. Goodrich. Examples of commercially available copolymers of the second type useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/C10–30 alkyl acrylate crosspolymers and are commerically available as Carbopol® 1342, Pemulen TR-1, and Pemulen TR-2, from B.F. Goodrich. Other optional copolymers of acrylic acid crosslinked with polyallyl sucrose are provided by B.F. Goodrich Company as, for example, Carbopol 934, 940, 941, and 956.

A carboxyvinyl polymer is an interpolymer of a monomeric mixture comprising a monomeric olefinically unsaturated carboxylic acid, and from about 0.01% to about 10% by weight of the total monomers of a polyether of a polyhydric alcohol, which polyhydric alcohol contains at least four carbon atoms to which are attached at least three hydroxyl groups, the polyether containing more than one alkenyl group per molecule. Other monoolefinic monomeric materials can be present in the monomeric mixture if desired, even in predominant proportion. Carboxyvinyl polymers are substantially insoluble in liquid, volatile organic hydrocarbons and are dimensionally stable on exposure to air.

Preferred polyhydric alcohols used to produce carboxyvinyl polymers include polyols selected from the class consisting of oligosaccharides, reduced derivatives thereof in which the carbonyl group is converted to an alcohol group, and pentaerythritol; more preferred are oligosaccharides, most preferred is sucrose. It is preferred that the hydroxyl groups of the polyol which are modified be etherified with allyl groups, the polyol having at least to allyl ether groups per polyol molecule. When the polyol is sucrose, it is preferred that the sucrose have at least about five allyl ether groups per sucrose molecule. It is preferred that the polyether of the polyol comprise from about 0.01% to about 4% of the total monomers, more preferably from about 0.02% to about 2.5%.

Preferred monomeric olefinically unsaturated carboxylic acids for use in producing carboxyvinyl polymers used herein include monomeric, polymerizable, alpha-beta monoolefinically unsaturated lower aliphatic carboxylic acids; more preferred are monomeric monoolefinic acrylic acids of the structure:

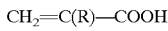

where R is a substituent selected from the group consisting of hydrogen and lower alkyl groups; most preferred is acrylic acid.

Preferred carboxyvinyl polymers used in formulations of the present invention have a molecular weight of at least about 750,000; more preferred are carboxyvinyl polymers having a molecular weight of at least about 1,250,000; most preferred are carboxyvinyl polymers having a molecular weight of at least about 3,000,000.

The anionic cellulosic thickeners can also include carboxymethyl cellulose and the like.

Nonionic cellulosic thickeners include, but are not limited to: 1. hydroxyethyl cellulose; 2. hydroxymethyl cellulose; 3. hydroxypropyl cellulose; and/or 4. hydroxybutyl methyl cellulose.

A suitable thickener is hydroxy ethyl cellulose, e.g., Natrosol® 250 KR sold by The Aqualon Company.

Other thickeners useful herein include acrylated steareth-20 methylacrylate copolymer sold as Acrysol® ICS-1 by Rohm and Haas Company; the carboxylic polymers disclosed in U.S. Pat. No. 5,318,774, Alban and Deckner, issued Jun. 7, 1994 (said patent being incorporated herein by reference); inorganic salts, i.e., chloride, sulfates, etc., at a level of from about 0.1% to about 5%, preferably from about 0.5% to about 3%; and fatty acids and fatty alcohols at a level of from about 1% to about 15%, preferably from about 2% to about 10%.

The liquid personal cleansing products can be thickened by using polymeric additives that hydrate, swell or molecularly associate to provide body (e.g., hydroxypropyl guar gum).

Liquid personal cleansing products, e.g., the liquid soap described hereinbefore, can be made with from about 0.1% to about 5%, preferably from about 0.3% to about 3%, of a cationic polymer, having a molecular weight of from about 1,000 to about 5,000,000, especially those selected from the group consisting of:

(I) cationic polysaccharides;
(II) cationic copolymers of saccharides and synthetic cationic monomers, and
(III) synthetic polymers selected from the group consisting of:
  (A) cationic polyalkylene imines;
  (B) cationic ethoxy polyalkylene imines; and
  (C) cationic poly[N-[-3-(dimethylammonio)propyl]-N'-[3-(ethyleneoxyethylene dimethylammonio) propyl]urea dichloride].

Detailed lists of suitable cationic polymers are set out in Small et al. and Medcalf et al., incorporated herein by reference.

Other materials can also be used as optional suspension agents include those that can impart a gel-like viscosity to the composition, such as water soluble or colloidally water soluble polymers like cellulose ethers (e.g., hydroxyethyl cellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Another type of suspending agent that can be used is xanthan gum. Xanthan gum is biosynthetic gum material that is commercially available. It is a heteropolysaccharide with a molecular weight of greater than 1 million. It is believed to contain D-glucose, D-mannose and D-glucuronate in the molar ratio of about 2.8:2.0:2.0. The polysaccharide is partially acetylated with about 4.7% acetyl. This information and other is found in Whistler, Roy L. Editor Industrial Gums—Polysaccharides and Their Derivatives New York: Academic Press, 1973. Kelco, a Division of Merck & Co., Inc., offers xanthan gum as Keltrol®. The gum, when used as a silicone hair conditioning component suspending agent, will typically be present in pourable, liquid formulations at a level of from about 0.02% to about 3%, preferably from about 0.03% to about 1.2%, in the compositions of the present invention.

In general, the level of optional suspending agent and other viscosity modifiers should preferably be as low as possible to achieve the benefit for which the material is added. Optional suspending agent thickeners, and viscosity modifiers, etc., when used are in general used at a level of from about 0.01% to about 10%, most commonly from about 0.02% to about 5.0%, preferably from about 0.1% to about 2%, and more preferably from about 0.2% to about 1.0% by weight of the total composition.

3. Water

The shampoo compositions of the present invention typically comprise from about 40% to about 89%, preferably from about 50% to about 85%, more preferably from about 60% to about 80%, by weight, of water.

The pH of the shampoo compositions hereof is not generally critical and can be in the range of from 2 to about 10, preferably from about 3 to about 9, more preferably from about 4 to about 8, most preferably from about 5.5 to about 7.5.

4. Insoluble Emulsified, Fluid Hair Conditioning Agent

The present compositions will optionally comprise from about 0.05% to about 10%, preferably from about 0.1% to about 8%, more preferably from about 0.2% to about 5%, by weight, of a dispersed phase, i.e., an emulsion, of a water-insoluble, nonvolatile, fluid hair conditioning agent. This component will be suspended in the form of droplets, which form a separate, discontinuous phase from the aqueous, continuous phase of the compositions. Number average droplet size is not critical to the invention, but is typically up to about 30 microns, preferably up to about 25 microns, and will typically be at least about 0.1 microns, more typically at least about 1 microns. Suitable fluid hair conditioning agents of this type include nonvolatile silicone hair conditioning agents and organic fluids, e.g., oils. This type of conditioning agent is a preferred ingredient. It has also been found that the surfactant system of the present invention can improve deposition for this type of conditioning agent when suspended by a crystalline suspending agent, as well as for the anti-dandruff agents.

By "nonvolatile" what is meant is that the liquid exhibits very low or no significant vapor pressure at ambient conditions (e.g., 25° C.), as is understood in the art, in general, less than 0.2 mm Hg (preferably less than 0.1 mm) at 25° C. The nonvolatile oil preferably has a boiling point at ambient pressure of about 250° C. or higher, more preferably about 275° C. or higher, most preferably about 300° C. or higher. Mixtures of the conditioning agents can be used. Individual components of the conditioning agent which are miscible may fall outside the boiling point limits, as long as the overall conditioning agent is nonvolatile as defined above.

By "water insoluble" what is meant is that the material is not soluble in water (distilled or equivalent) at a concentration of 0.1%, at 25° C.

5. Silicone Hair Conditioning Agent

The non-volatile, water insoluble silicone hair conditioning agent component of the present invention is nonvolatile and insoluble in the composition. It will be intermixed in the shampoo composition so as to be in the form of an emulsion, i.e., a separate, discontinuous phase of dispersed, insoluble droplets. These droplets are suspended with a suspending agent, numerous, non-exclusive suitable examples of which are described below. This dispersed silicone conditioning component will comprise a silicone fluid hair conditioning agent such as a silicone fluid and can also comprise other ingredients, such as a silicone resin to enhance silicone fluid deposition efficiency or enhance glossiness of the hair (especially when high refractive index (e.g., above about 1.46) silicone conditioning agents are used (e.g., highly phenylated silicones).

The silicone hair conditioning agent phase can comprise volatile silicone components. Typically, if volatile silicones are present, it will be incidental to their use as a solvent or carrier for commercially available forms of nonvolatile silicone materials ingredients, such as silicone gums and resins.

The silicone hair conditioning agent component for use herein will preferably have a viscosity of from about 20 to about 2,000,000 centistokes at 25° C., more preferably from about 1,000 to about 1,800,000, even more preferably from about 50,000 to about 1,500,000, most preferably from about 100,000 to about 1,500,000. The viscosity can be measured by means of a glass capillary viscometer as set forth in Dow Corning Corporate Test Method CTM0004, Jul. 20, 1970.

The silicone hair conditioning agent component will generally be used in the shampoo compositions hereof at levels of from about 0.05% to about 10% by weight of the composition, preferably from about 0.1% to about 8%, more preferably from about 0.2% to about 5%, most preferably from about 0.5% to about 4%. The minimum level that is used in a particular composition should be effective to provide a conditioning benefit. The maximum level that can be used is not limited by theory, but rather by practicality. It is generally unnecessary and expensive to use levels in excess of about 8%, although higher levels can be used if desired.

One type of silicone fluid that can be used herein is a silicone oil. The term "silicone oil" shall mean flowable silicone materials having a viscosity of less than about 1,000,000 centistokes at 25° C. Generally, the viscosity of the fluid will be between about 5 and about 1,000,000 centistokes at 25° C., preferably between about 10 and about 100,000. Suitable silicone oils include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used.

More particularly silicone oils hereof include polyalkyl or polyaryl siloxanes with the following structure (IX):

$$R-Si(R)_2-O-[-Si(R)_2-O-]_x-Si(R)_2-R \qquad (IX)$$

wherein R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic and/or aryl groups substituted on the siloxane chain can have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, are insoluble in the composition, and are capable of being deposited on and, of conditioning, the hair.

The two R groups on the silicon atom of each monomeric silicone unit can represent the same group or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g., alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g., chloride, fluoride, and bromide), halogenated aliphatic or aryl groups, and hydroxy (e.g., hydroxy substituted aliphatic groups). Suitable halogenated R groups could include, for example, tri-halogenated (preferably fluoro) alkyl groups such as $-R^1-C(F)_3$, wherein $R^1$ is $C_1$–$C_3$ alkyl. Examples of such polysiloxanes include polymethyl-3,3,3 trifluoropropylsiloxane.

The nonvolatile polyalkylsiloxane fluids that can be used include, for example, polydimethylsiloxanes. These siloxanes are available, for example, from the General Electric Company in their Viscasil R and SF 96 series, and from Dow Corning in their Dow Corning 200 series.

Other suitable R groups include methyl, methoxy, ethoxy, propoxy, and aryloxy. The three R groups on the end caps of the silicone can also represent the same or different groups.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

The polyalkylaryl siloxane fluids that can be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that can be used include, for example, a polypropylene oxide modified polydimethylsiloxane (e.g., Dow Corning DC-1248) although ethylene oxide or mixtures of ethylene oxide and propylene oxide can also be used. The ethylene oxide and polypropylene oxide level must be sufficiently low to prevent solubility in water and the composition hereof.

Alkylamino substituted silicones that can be used herein include those of the formula:

$$HO-[Si(CH_3)_2O]_x-[Si(OH)[(CH_2)_3NH(CH_2)_2NH_2]O]_y-H$$

in which x and y are integers which depend on the molecular weight, the average molecular weight being approximately between 5,000 and 10,000. This polymer is also known as "amodimethicone".

Cationic silicone fluids which can be used in the present compositions include those that correspond to the formula:

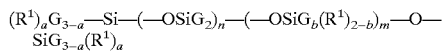

in which G is chosen from the group consisting of hydrogen, phenyl, OH, $C_1$–$C_8$ alkyl and preferably methyl; a denotes 0 or an integer from 1 to 3, and preferably equals 0;

b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R^1$ is a monovalent radical of formula $C_qH_{2q}L$ in which q is an integer from 2 to 8 and L is chosen from the groups:

—N($R^2$)CH$_2$—CH$_2$—N($R^2$)$_2$

—N($R^2$)$_2$

—N$^+$$R^2$)$_3$A$^-$

—N$^+$($R^2$)CH$_2$—CH$_2$—N$^+$($R^2$)$_3$A$^-$ in which each $R^2$ is chosen from the group consisting of hydrogen, phenyl, benzyl, a saturated hydrocarbon radical, preferably an alkyl radical containing from 1 to 20 carbon atoms, and A$^-$ denotes a halide ion.

An especially preferred cationic silicone corresponding to the formula immediately above is the polymer known as "trimethylsilylamodimethicone," of formula (X):

(CH$_3$)$_3$—SiO—[Si(CH$_3$)$_2$O]$_n$—[Si(CH$_3$)[(CH$_2$)$_3$NH(CH$_2$)$_2$NH$_2$]O]$_m$—Si(CH$_3$)$_3$     (X)

Other cationic silicone polymers which can be used in the present compositions correspond to the formula (XI):

($R^3$)$_3$SiO—[Si(CH$_3$)[R$_4$CH$_2$CHOHCH$_2$N$^+$($R^3$)$_3$Q$^-$]O]$_r$—[Si(CH$_3$)$_2$O]$_s$—Si($R^3$)$_3$     (XI)

in which each $R^3$ denotes a monovalent hydrocarbon radical having from 1 to 18 carbon atoms, and more especially an alkyl or alkenyl radical such as methyl; Q$^-$ is a halide ion, preferably chloride;

r denotes an average statistical value from about 2 to about 20, preferably from about 2 to about 8;

s denotes an average statistical value from about 20 to about 200, and preferably from about 20 to about 50.

These compounds are described in greater detail in U.S. Pat. No. 4,185,017, incorporated herein by reference.

A polymer of this class which is especially preferred is that sold by Union Carbide under the name "UCAR Silicone ALE 56".

Another silicone fluid that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979, and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane oil having a viscosity of from about 10 centistokes to about 100,000 centistokes, wherein the ratio of gum to fluid is from about 30:70 to about 70:30, preferably from about 40:60 to about 60:40.

Another category of nonvolatile, insoluble silicone fluid conditioning agents are high refractive index silicones, having a refractive index of at least about 1.46, preferably at least about 1.48, more preferably at least about 1.52, most preferably at least about 1.55. Although not intended to necessarily be limiting, the refractive index of the polysiloxane fluid will generally be less than about 1.70, typically less than about 1.60. Polysiloxane "fluid" includes oils as well as gums.

The high refractive index polysiloxane fluid suitable for purposes hereof includes those represented by general Formula (IX) above, as well as cyclic polysiloxanes such as those represented by the formula below:

wherein R is as defined above, n is from about 3 to about 7, preferably from 3 to 5.

The high refractive index polysiloxane fluids hereof contain a sufficient amount of aryl-containing R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$–$C_5$ alkyl or alkenyl substituents, e.g., allylphenyl, methyl phenyl and ethyl phenyl, vinyl phenyls such as styrenyl, and phenyl alkynes (e.g., phenyl $C_2$–$C_4$ alkynes). Heterocyclic aryl groups include substituents derived from furan, imidazole, pyrrole, pyridine, etc. Fused aryl ring substituents include, for example, napthalene, coumarin, and purine.

In general, the high refractive index polysiloxane fluids hereof will have a degree of aryl-containing substituents of at least about 15%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

These polysiloxane fluids are also characterized by relatively high surface tensions as a result of their aryl substitution. In general, the polysiloxane fluids hereof will have a surface tension of at least about 24 dynes/cm$^2$, typically at least about 27 dynes/cm$^2$. Surface tension, for purposes hereof, is measured by a de Nouy ring tensiometer according to Dow Corning Corporate Test Method CTM 0461, Nov. 23, 1971. Changes in surface tension can be measured according to the above test method or according to ASTM Method D 1331.

The preferred high refractive index polysiloxane fluids hereof will have a combination of phenyl or phenyl derivative substituents (preferably phenyl), with alkyl substituents, preferably $C_1$–$C_4$ alkyl (most preferably methyl), hydroxy, $C_1$–$C_4$ alkylamino (especially —$R^1NHR^2NH_2$ where each $R^1$ and $R^2$ independently is a $C_1$–$C_3$ alkyl), alkenyl, and/or alkoxy.

High refractive index polysiloxane are available commercially from Dow Corning Corporation (Midland, Mich., U.S.A.) Hüls America (Piscataway, N.J., U.S.A.), and General Electric Silicones (Waterford, N.Y., U.S.A.).

It is preferred to utilize high refractive index silicones in solution with a spreading agent, such as a silicone resin or a surfactant, to reduce the surface tension by a sufficient amount to enhance spreading and thereby enhance glossiness (subsequent to drying) of hair treated with the composition. In general, a sufficient amount of the spreading agent to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture can provide improved shine enhancement of the hair.

Also, the spreading agent will preferably reduce the surface tension by at least about 2 dynes/cm$^2$, preferably at least about 3 dynes/cm$^2$, even more preferably at least about 4 dynes/cm$^2$, most preferably at least about 5 dynes/cm$^2$.

The surface tension of the mixture of the polysiloxane fluid and the spreading agent, at the proportions present in the final product, is preferably 30 dynes/cm$^2$ or less, more preferably about 28 dynes/cm$^2$ or less most preferably about 25 dynes/cm$^2$ or less. Typically the surface tension will be in the range of from about 15 to about 30, more typically from about 18 to about 28, and most generally from about 20 to about 25 dynes/cm$^2$.

The weight ratio of the highly arylated polysiloxane fluid to the spreading agent will, in general, be between about 1000:1 and about 1:1, preferably between about 100:1 and about 2:1, more preferably between about 50:1 and about 2:1, most preferably from about 25:1 to about 2:1. When fluorinated surfactants are used, particularly high polysiloxane: spreading agent ratios can be effective due to the efficiency of these surfactants. Thus is contemplated that ratios significantly above about 1000:1 can be used.

Incorporated herein by reference is Silicon Compounds distributed by Petrarch Systems, Inc., 1984. This reference provides an extensive (though not exclusive) listing of suitable silicone fluids.

An optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp. 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to the presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below about 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e., the conditioning active, the sum of the fluid and resin should be included in determining the level of conditioning agent in the composition.

Silicones which can be utilized in the compositions of the present invention include those described in U.S. Pat. No. 5,154,849, Visscher et al., which is herein incorporated by reference.

6. Organic Hair Conditioning Agent

The organic fluid hair conditioning agents hereof generally will have a viscosity of about 3 million cS or less, preferably about 2 million cS or less, more preferably about 1.5 million cS or less (as measured by a Bohlin VOR Rheometer, or equivalent). For purposes hereof, "organic" shall not include silicone hair conditioning agents.

The organic hair conditioning materials hereof include fluids selected from the group consisting of hydrocarbon fluids and fatty esters. The fatty esters hereof are characterized by having at least 10 carbon atoms, and include esters with hydrocarbyl chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon fluids include oils such as cyclic hydrocarbons, straight chain aliphatic hydrocarbons (saturated or unsaturated), and branched chain aliphatic hydrocarbons (saturated or unsaturated), and mixtures thereof. Straight chain hydrocarbon oils will preferably contain from about 12 to about 19 carbon atoms, although it is not necessarily meant to limit the hydrocarbons to this range. Branched chain hydrocarbon oils can and typically can contain higher numbers of carbon atoms. Also encompassed herein are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 500, preferably from about 200 to about 400, more preferably from about 300 to about 350. Specific examples of suitable materials include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eiocosane, such as 2,2,4,4,6,6,8,8-dimethyl-10-methylundecane and 2,2,4,4,6,6-dimethyl-8-methylnonane, sold by Permethyl Corporation. Polymeric organic materials are also useful conditioning agents. A preferred organic polymer is polybutene, such as the copolymer of isobutylene and butene. A commercially available material of this type if L-14 polybutene from Amoco Chemical Co. (Chicago, Ill., U.S.A.). Other polymeric conditioners can include polyisoprene, polybutadiene, and other hydrocarbon polymers of $C_4$ to $C_{12}$ straight and branched chain, mono- and di-unsaturated aliphatic monomers, and derivatives thereof.

Monocarboxylic acid esters hereof include esters of alcohols and/or acids of the formula R'COOR wherein alkyl or alkenyl radicals and the sum of carbon atoms in R' and R is at least 10, preferably at least 20.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof Examples include isopropyl isostearate, hexyl laurate, isohexyl laurate, iso-hexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

The mono-carboxylic acid ester however need not necessarily contain at least one chain with at least 10 carbon atoms, so long as the total number of aliphatic chain carbon atoms is at least 10. Examples include diisopropyl adipate, diisohexyl adipate, and diisopropyl sebacate.

Di- and tri-alkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Specific example include isocetyl stearoyl stearate, diisopropyl adipate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

Glycerides include mono-, di-, and tri-glycerides. More specifically, included are the mono-, di-, and tri-esters of glycerol and long chain carboxylic acids, such as $C_1$–$C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include triolein and tristearin glyceryl dilaurate. Preferred glycerides are di-, and tri-glycerides. Especially preferred are triglycerides.

7. Other Optional Ingredients, Primarily for Shampoo Compositions

A variety of other optional ingredients are described below. The description below is exemplary in nature.

Such optional ingredients include, for example, anti-dandruff actives such as zinc pyrithione, octopirox, selenium disulfide, sulfur, coal tar, and the like, preservatives such as benzyl alcohol, methyl paraben, propyl paraben and imidazolidinyl urea; cationic conditioning agents, including both cationic conditioning surfactants and cationic conditioning polymers; quaternary polymeric foam boosters, such as Polyquaternium 10, preferably from about 0.01% to about 0.2%, by weight of the composition; fatty alcohols; block polymers of ethylene oxide and propylene oxide such as Pluronic F88 offered by BASF Wyandotte; sodium chloride, sodium sulfate; ammonium xylene sulfonate; propylene glycol; polyvinyl alcohol; ethyl alcohol; pH adjusting agents such as citric acid, succinic acid, phosphoric acid, sodium hydroxide, sodium carbonate, etc.; perfumes; and dyes. These optional ingredients are typically used at levels of from about 0.01% to about 10% of the composition. The shampoo compositions herein can also contain a builder, but preferably less than about 1%, or none at all. This list of optional ingredients is not meant to be exclusive, and other optional components can be utilized.

8. Other Optional Ingredients Primarily for Non-Shampoo Compositions

Another component useful in the present invention is a nonionic, i.e., polyglycerol ester (PGE).

Groups of substances which are particularly suitable for use as nonionic surfactants are alkoxylated fatty alcohols or alkylphenols, preferably alkoxylated with ethylene oxide or mixtures of ethylene oxide or propylene oxide; polyglycol esters of fatty acids or fatty acid amides; ethylene oxide/propylene oxide block polymers; glycerol esters and polyglycerol esters; sorbitol and sorbitan esters; polyglycol esters of glycerol; ethoxylated lanolin derivatives; and alkanolamides and sucrose esters.

A preferred liquid cleansing composition also contains from about 0.5% to about 10% of an emollient selected from the group consisting of esters of fatty acids; glycerin mono-, di-, and tri-esters; epidermal and sebaceous hydrocarbons such as cholesterol, cholesterol esters, squalene, squalane; lanolin and derivatives, mineral oil, silicone oils and gums, and mixtures thereof and the like.

Other ingredients of the present invention are selected for the various applications. E.g., alcohols, hydrotropes, colorants, and fillers such as talc, clay, calcium carbonate and dextrin can also be used. Cetearyl alcohol is a mixture of cetyl and stearyl alcohols. Preservatives, e.g., trisodium etidronate and sodium ethylenediaminetetraacetate (EDTA), generally at a level of less than 1% of the composition, can be incorporated in the cleansing products to prevent color and odor degradation. Antibacterials can also be incorporated, usually at levels up to 1.5%. Salts, both organic and inorganic, can be incorporated into the compositions of the present invention. Examples include sodium chloride, sodium isethionate, sodium sulfate, and their equivalents.

The cleansing bath/shower compositions can contain a variety of nonessential optional ingredients suitable for rendering such compositions more desirable. Such conventional optional ingredients are well known to those skilled in the art, e.g., preservatives such as benzyl alcohol, methyl paraben, propyl paraben and imidazolidinyl urea; other thickeners and viscosity modifiers such as $C_8$–$C_{18}$ ethanolamide (e.g., coconut ethanolamide) pH adjusting agents such as citric acid, succinic acid, phosphoric acid, sodium hydroxide, etc.; suspending agents such as magnesium/aluminum silicate; perfumes; dyes; and sequestering agents such as disodium ethylenediamine tetraacetate.

III. Method Of Use For Shampoo Compositions

The present compositions are used in a conventional manner for cleaning hair, controlling dry skin on the scalp, and to provide olfactory aesthetic benefit. The compositions hereof can also be effective for cleaning the skin (e.g., the body in general, including the underarm and crotch areas). An effective amount of the composition, typically from about 1 g to about 20 g of the composition, for cleaning hair or other region of the body, is applied to the hair or other region that has preferably been wetted, generally with water, and then rinsed off. Application to the hair typically includes working the composition through the hair such that most or all of the hair is contacted with the composition. After the rinse step, the wet hair is normally dried, e.g., with an electric hair dryer.

IV. Method Of Use For Personal Cleansing Non-Shampoo Compositions

The present compositions are used in a conventional manner for cleaning the skin and/or the body, and to provide olfactory aesthetic benefit. An effective amount of the composition, typically from about 1 g to about 15 g of the composition, is applied to the body that has preferably been wetted, generally with water. Application to the body includes dispensing of the composition onto the hand, onto the body, or onto a washing implement, e.g., wash cloth, sponge, etc., and typically includes working the composition with the hands to develop lather. The lather can stand on the body for a length of time or can be rinsed immediately with water. Once the product is rinsed from the body the washing procedure can be repeated.

C. Hair Care And Topical Skin Care Compositions Which Are Not Normally Rinsed (Removed)

The enduring perfumes of the present invention can be formulated into a wide variety of product types which are not normally removed by rinsing, including hair conditioner, hair spray, hair gel, hair tonic, mousse, hair curler, hair straightener, deodorant, antiperspirant, skin lotion, skin moisturizer, skin softening lotion, suntan lotion, sun screen lotion, sunless tanning composition, skin bleaching composition, perfume, cologne, topical pharmaceutical skin care composition, e.g., anti-acne composition, non-steroidal anti-flammatory composition, steroidal anti-flammatory composition, antipruritic composition, anesthetic composition, antimicrobial composition, and the like. The additional components required to formulate such products vary with product type and can be routinely chosen by one skilled in the art. The following is a description of some of these compositions and additional components.

I. Hair Care Compositions

The hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Carriers suitable for use with hair care compositions of the present invention include, for example, those used in the formulation of hair sprays, mousses, tonics, gels, conditioners, and rinses. The choice of appropriate carrier will also depend on the particular copolymer to be used, and whether the product formulated is meant to be left on the surface to which it is applied (e.g., hair spray, mousse, tonic, or gel) or rinsed off after use (e.g., conditioner, rinse).

The carriers used herein can include a wide range of components conventionally used in hair care compositions. The carriers can contain a solvent to dissolve or disperse the particular copolymer being used, with water, the $C_1$–$C_6$ alcohols, and mixtures thereof being preferred; and water, methanol, ethanol, isopropanol, propylene carbonate, and mixtures thereof being more preferred. The carriers can also contain a wide variety of additional materials including, but not limited to, acetone, hydrocarbons (such as isobutane, hexane, decene), halogenated hydrocarbons (such as Freons), esters (such as ethyl acetate, dibutyl phthalate), and volatile silicon derivatives (especially siloxanes such as phenyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane, cyclomethicone, and dimethicone having for example, a viscosity at 25° C. of about 15 centipoise or less), and mixtures thereof. When the hair care composition is a hair spray, tonic, gel, or mousse the preferred solvents include water, ethanol, volatile silicone derivatives, and mixtures thereof. The solvents used in such mixtures can be miscible or immiscible with each other. Mousses and aerosol hair sprays can also utilize any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity can also utilize an emulsifying agent. Examples of suitable emulsifying agents include nonionic, cationic, anionic surfactants, or mixtures thereof. Fluorosurfactants are especially preferred, particularly if the product is a hair spray composition and most especially if it is a spray composition having relatively low levels of volatile organic solvents, such as alcohols, and relatively high levels of water (e.g., in excess of about 10%, by weight water). If such an emulsifying agent is used, it is preferably present at a level of from about 0.01% to about 7.5% of the composition. The level of propellant can be adjusted as desired but is generally from about 3% to about 30% of mousse compositions and from about 15% to about 50% of the aerosol hair spray compositions.

Suitable spray containers are well known in the art and include conventional, non-aerosol pump sprays i.e., "atomizers," aerosol containers or cans having propellant, as described above, and also pump aerosol containers utilizing compressed air as the propellent. Pump aerosol containers are disclosed, for example, in U.S. Pat. Nos. 4,077,441, Mar. 7, 1978, Olofsson and 4,850,577, Jul. 25, 1989, TerStege, both incorporated by reference herein, and also in U.S. Ser. No. 07/839,648, Gosselin, Lund, Sojka, and Lefebvre, filed Feb. 21, 1992, "Consumer Product Package Incorporating A Spray Device Utilizing Large Diameter Bubbles." Pump aerosols hair sprays using compressed air are also currently marketed by The Procter & Gamble Company under their tradename Vidal Sassoon Airspray® hair sprays.

Where the hair care compositions are conditioners and rinses the carrier can include a wide variety of conditioning materials. Various additional components useful in hair care compositions are described in U.S. Pat. No. 5,106,609, to Bolich, Jr. et al., issued Apr. 21, 1992; and U.S. Pat. No. 4,387,090, to Bolich, Jr. issued Jun. 7, 1983; which are incorporated by reference herein. Some of these additional components are described below.

II. Topical Skin Care Compositions

The topical cosmetic and pharmaceutical compositions of the present invention can comprise a carrier. The carrier should be "cosmetically and/or pharmaceutically acceptable", which means that the carrier is suitable for topical application to the skin, has good aesthetic properties, is compatible with the copolymers of the present invention and any other components, and will not cause any untoward safety or toxicity concerns.

The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g, from about 100 cps to about 200,000 cps. These emulsions can also be delivered in the form of sprays using either mechanical pump containers or pressurized aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like). Examples of topical carrier systems useful in the present invention are described in the following four references all of which are incorporated herein by reference in their entirety: "Sun Products Formulary" Cosmetics & Toiletries, vol. 105, pp. 122–139 (December 1990); "Sun Products Formulary", Cosmetics & Toiletries, vol. 102, pp. 117–136 (March 1987); U.S. Pat. No. 4,960,764 to Figueroa et al., issued Oct. 2, 1990; and U.S. Pat. No. 4,254,105 to Fukuda et al., issued Mar. 3, 1981.

The carriers of the skin care compositions can comprise from about 50% to about 99% by weight of the compositions of the present invention, preferably from about 75% to about 99%, and most preferably from about 85% to about 95%.

Preferred cosmetically and/or pharmaceutically acceptable topical carriers include hydro-alcoholic systems and oil-in-water emulsions. When the carrier is a hydro-alcoholic system, the carrier can comprise from about 1% to about 99% of ethanol, isopropanol, or mixtures thereof, and from about 1% to about 99% of water. More preferred is a carrier comprising from about 5% to about 60% of ethanol, isopropanol, or mixtures thereof, and from about 40% to about 95% of water. Especially preferred is a carrier comprising from about 20% to about 50% of ethanol, isopropanol, or mixtures thereof, and from about 50% to about 80% of water. When the carrier is an oil-in-water emulsion, the carrier can include any of the common excipient ingredients for preparing these emulsions. In fine fragrances, the carrier is typically ethanol at levels of from about 50% to about 85%, whereas in colognes, the carrier level is even higher, e.g., from about 80% to about 95%.

III. Antiperspirant and/or Deodorant Compositions

1. Carriers

Carriers for antiperspirants and deodorants are well known in the art. Some particularly desirable ones are disclosed in U.S. Pat. No. 4,944,937, McCall, issued Jul. 31, 1990, especially at Col. 2, line 51 through Col. 7, line 11 (Cosmetic Sticks); U.S. Pat. No. 4,985,238, Tanner, Nunn, Jr., and Luebbe, issued Jan. 15, 1991, especially at Col. 2, line 41 through Col. 3, line 32 and Col. 5, line45 through Col. 6, line 31 (Low Residue Antiperspirant Sticks); U.S. Pat. No. 5,019,375, Tanner, Nunn, Jr., and Luebbe, issued May 28, 1991, especially at Col. 3, line 16 through Col. 3, line 35 and Col. 4, line 64 through Col. 7, line 10 (Low Residue Antiperspirant Creams); U.S. Pat. No. 5,069,897, Orr, issued Dec. 3, 1991, especially at Col. 3, line 1 through Col. 4, line 49 and Col. 5, line 65 through Col. 6, line 64 (Antiperspirant Creams); U.S. Pat. No. 5,156,834, Beckmeyer, Davis, and Kelm, issued Oct. 20 1992, especially at Col. 4, line 8 through Col. 5, line 64 (Anitperspirant Compositions); U.S. Pat. No. 5,200,174, Gardlik and Hofrichter, issued Aug. 6 1993, especially at Col. 5, line 16 through Col. 7, line 34 and Col. 10, line 24 through Col. 12, line 44 (Gel Stick Antiperspirant Composition Containing 2-Oxazolidinone Derivative and Process for Making Them); U.S. Pat. No. 5,284,649, Juneja, issued Feb. 8, 1994, especially at Col. 3, line 55 through Col. 5, line 42 (Deodorant Gel Sticks Containing 1-Hydroxy Pyridinethione Active); and U.S. Pat. No. 5,298,326, Orr and Newcomer, issued Mar. 29, 1994, especially at Col. 6, line 14 through Col. 8, line 21 (Liquid Antiperspirant Composition), all of said patents being incorporated herein by reference. These patents also disclose many of the other ingredients that are useful in antiperspirant and deodorant products.

Some antiperspirant gel stick compositions of the present invention include the ingredients discussed below. Although the term "stick" as utilized herein includes semi-solid forms (i.e., preferably having a viscosity of at least about 1,000,000 centipoise at 25° C.), solid forms (i.e., preferably having an average penetration value within a given production batch from about 3 to about 25 mm over a period of 5 seconds as measured utilizing American Society for Testing Materials (ASTM) Method D-5, with a penetration cone (Model H1312; sold by Humbolt Manufacturing Company) weighing 2.0 g (making the total mass 50 g and a Sommer & Runge Model PNR10 Penetrometer) are preferred.

2. Gelling Agent

The "gelling agent" as used herein is a mixture of a primary gellant and a secondary gellant; both discussed hereinafter. The primary gellant is selected from the group consisting of 12-hydroxystearic acid, esters of 12-hydroxystearic acid, amides of 12-hydroxystearic acid and mixtures thereof. The secondary gellant is selected from the group consisting of n-acyl amino acid derivatives. The level of the gelling agent within the composition is typically from about 1% to about 15%; preferably, from about 3% to about 12%; more preferably, from about 5% to about 10%. The primary gellant:secondary gellant ratio is typically between about 1:2 and about 20:1; preferably, from about 1:1 to about 10:1; more preferably, from about 2:1 to about 7:1; and even more preferably, from about 3:1 to about 5:1. The primary gellant:secondary gellant ratio appears to be more critical when the level of polar, non-volatile liquid within the liquid base material (discussed hereinafter) in the composition is relatively low; e.g., below about 25%.

This gelling agent offers significant benefits when used in an antiperspirant gel stick. The gelling agent of the present invention exhibits unexpected benefits, e.g., decreased residue upon application to the skin, increased hardness and better aesthetics, relative to a similar composition having either of the two gellants alone. In fact, these gellants in combination are more effective than either alone so that the overall level of gelling agent within the composition can be reduced while maintaining such desirable stick characteristics.

Moreover, when these gellants are used together as the gelling agent of the present invention, degradation of the gelling agent by the acidic antiperspirant active during manufacturing is unexpectedly significantly reduced; i.e., as compared to each gellant alone. To further reduce degradation, a heated solution of the gelling agent and the liquid base material preferably remains in solution such that the antiperspirant active can be substantially uniformely mixed therein at a temperature less than about 120° C.; more preferably, less than about 105° C.; more preferably, less than about 95° C.; and most preferably, less than about 80° C. (hereinafter, the "mixing temperature"). This reduced mixing temperature is made possible partly because the primary gellant, once molten, is an unexpectedly good co-solvent for the secondary gellant, thereby facilitating their dissolution at a lower temperature. Additional methods of reducing the mixing temperature or otherwise enabling a reduction of the interaction of the acidic antiperspirant active with other components, e.g., the gelling agent, is discussed hereinafter. Since lower mixing temperatures can be utilized, the gelling agent is more compatible with additional gel stick components which have lower boiling points, such as perfumes.

a. Primary Gellant

The primary gellant of the gelling agent of the present invention is selected from the group consisting of 12-hydroxystearic acid, esters of 12-hydroxystearic acid, amides of 12-hydroxystearic acid and mixtures thereof. The primary gellant is preferably selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof; even more preferably, 12-hydroxystearic acid, isopropyl amide of 12-hydroxystearic acid, and mixtures thereof.

b. Secondary Gellant

With regard to the secondary gellant of the gelling agent of the present invention, N-acyl amino acid derivatives include N-acyl amino acid amides and N-acyl amino acid esters prepared from glutamic acid, lysine, glutamine, aspartic acid and mixtures thereof.

Preferably the N-acyl amino acid derivatives are selected from the group consisting of N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide and mixtures thereof, more preferred, is n-lauroyl-glutamic acid dibutyl amide, n-stearyl-glutamic acid dihexyl amide, and mixtures thereof.

3. Liquid Base Materials

The liquid base matrix of antiperspirant stick compositions of the present invention is formed by combining the gelling agent with a liquid base material. As used herein, the term "liquid" refers to materials which are liquids at ambient conditions and the term "liquid base material" includes all liquids within the composition. It is important that the liquid base material be of a type, and used at a level sufficient to solubilize the gelling agent when heated, to permit substantially uniform mixing of the antiperspirant active into the heated solution at the mixing temperature, and form a stick when cooled to ambient temperature. The liquid base material should be compatible with the gelling agent so that the mixture of the two remains homogeneous and does not phase separate during manufacturing and so that the finished product remains homogeneous and does not phase separate at ambient conditions over the normal shelf-life which may be upwards of one year. Furthermore, the liquid base materials are typically selected to provide aesthetic benefits, such as emolliency, low tack or minimized visible residue, without significant interference with the effectiveness of the antiperspirant active component. Lastly, the particular liquid base material should be safe for application to human skin.

The liquid base materials include emollients which have a solubility parameter from about 5 to about 11. It is preferable that, in aggregate, the average solubility parameter of the liquid base material be from about 6 to about 10. Hence, a mixture of emollients may be used as the liquid base material herein, each having a solubility parameter in the range of from about 5 to about 11, such that the average solubility parameter of the mixture is from about 6 to about 10. Solubility parameters are common to the art of antiperspirant stick formulation and the means to determine them are disclosed by C. D. Vaughan, "Solubility Effects in Product, Package, Penetration and Preservation" 103 Cosmetics and Toiletries 47–69, October, 1988; and C. D. Vaughan, "Using Solubility Parameters in Cosmetics Formulation", 36 J Soc. Cosmetic Chemists 319–333, September/October, 1985.

The liquid base material of the present invention is preferably used at levels from about 10% to about 95%; and more preferably from about 45% to about 80%. The liquid base material preferably includes a volatile, non-polar, oil and a non-volatile, relatively polar co-solvent; each discussed more fully hereinafter. The term "non-volatile" as used herein refers to materials which exhibit a vapor pressure of no more than about 0.2 mm Hg at 25° C. at one atmosphere and/or to materials which have a boiling point at one atmosphere of at least about 300° C. The term "volatile" as used herein refers to all materials which are not "non-volatile" as previously defined herein. The phrase "relatively polar" as used herein means more polar than another material in terms of solubility parameter; i.e., the higher the solubility parameter the more polar the liquid. The term "non-polar" typically means that the emollient has a solubility parameter below about 6.5.

a. Non-polar, Volatile Oil

The non-polar, volatile oil tends to impart highly desirable aesthetic properties to the gel stick. Consequently, the non-polar, volatile oils are preferably utilized at a fairly high level. Such non-polar, volatile oils are preferably used at levels from about 10% to about 70%; more preferably, from about 25% to about 60%; more preferably from about 40% to about 60%.

Non-polar, volatile oils particularly useful in the present invention are selected from the group consisting of silicone oils; hydrocarbons; and mixtures thereof. Such non-polar, volatile oils are disclosed, for example, in Cosmetics, Science, and Technology, Vol. 1, 27–104 edited by Balsam and Sagarin, 1972. The non-polar, volatile oils useful in the present invention may be either saturated or unsaturated, have an aliphatic character and be straight or branched chained or contain alicyclic or aromatic rings. Examples of preferred non-polar, volatile hydrocarbons include isodecane (such as Permethyl-99A® which is available from Presperse Inc.) and the $C_7$–$C_8$ through $C_{12}$–$C_{15}$ isoparaffins (such as the Isopar® Series available from Exxon Chemicals).

Non-polar, volatile silicone oils are highly preferred as the non-polar, volatile oil in the liquid base material, since they endow the antiperspirant stick composition with highly desirable aesthetics. Non-polar, volatile liquid silicone oils are disclosed in U.S. Pat. No. 4,781,917 issued to Luebbe et al. on Nov. 1, 1988. Additionally, a description of various volatile silicones materials is found in Todd et al., "Volatile Silicone Fluids for Cosmetics", Cosmetics and Toiletries, 91:27–32 (1976). Particularly preferred volatile silicone oils are cyclic and linear volatile silicones like those disclosed hereinbefore.

b. Relatively Polar, Non-volatile Co-solvent

The relatively polar co-solvent aids in the utilization of reduced processing temperatures by solubulizing at least one of the gellants and being soluble in the non-polar, volatile oil when subjected to reduced processing temperatures. The non-volatile co-solvent is "relatively polar" as compared to the non-polar, volatile oil discussed above. Therefore, the non-volatile co-solvent is more polar (i.e., has a higher solubility parameter) than at least one of the non-polar, volatile oils.

In addition to enabling reduced processing temperatures, the co-solvent enables the inclusion of greater amounts of the non-polar, volatile oil. This is advantageous because, as discussed above, the non-polar, volatile oil provides significant cosmetic benefits. The quantity of relatively polar, non-volatile co-solvent, however, is preferably kept to a minimum because it tends to adversely affect product cosmetics. Thus, the relatively polar, non-volatile co-solvent is preferably included at levels from about 5% to about 60%; more preferably from about 5% to about 25%; and most preferably from about 7% to about 20%.

Relatively polar, non-volatile liquids potentially useful as the co-solvent in the present invention are disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989. Relatively polar, non-volatile co-solvents useful in the present invention are preferably selected from the group consisting of silicone oils; hydrocarbon oils; fatty alcohols; fatty acids; esters of mono and dibasic carboxylic acids with mono and polyhydric alcohols, polyoxyethylenes; polyoxypropylenes; mixtures of polyoxyethylene and polyoxypropylene ethers of fatty alcohols; and mixtures thereof. The relatively polar, non-volatile co-solvents useful in the present invention may be either saturated or unsaturated, have an aliphatic character and be straight or branched chained or contain alicyclic or aromatic rings.

More preferably, the relatively polar, non-volatile liquid co-solvent are selected from the group consisting of fatty alcohols having from about 12–26 carbon atoms; fatty acids having from about 12–26 carbon atoms; esters of monobasic carboxylic acids and alcohols having from about 14–30 carbon atoms; esters of dibasic carboxylic acids and alcohols having from about 10–30 carbon atoms; esters of polyhydric alcohols and carboxylic acids having from about 5–26 carbon atoms; ethoxylated, propoxylated, and mixtures of ethoxylated and propoxylated ethers of fatty alcohols with from about 12–26 carbon atoms and a degree of ethoxylation and propoxylation of below about 50; and mixtures thereof More preferred are propoxylated ethers of $C_{14}$–$C_{18}$ fatty alcohols having a degree of propoxylation below about 50, esters of $C_2$–$C_8$ alcohols and $C_{12}$–$C_{26}$ carboxylic acids (e.g. ethyl myristate, isopropyl palmitate), esters of $C_{12}$–$C_{26}$ alcohols and benzoic acid (e.g. Finsolv TN® supplied by Finetex), diesters of $C_2$–$C_8$ alcohols and adipic, sebacic, and phthalic acids (e.g., diisopropyl sebacate, diisopropyl adipate, di-n-butyl phthalate), polyhydric alcohol esters of $C_6$–$C_{26}$ carboxylic acids (e.g., propylene glycol dicaprate/dicaprylate, propylene glycol isostearate); and mixtures thereof.

Even more preferred are branched-chain aliphatic fatty alcohols having from about 12–26 carbon atoms. Even more preferred is isocetyl alcohol, octyldecanol, octyldodecanol and undecylpentadecanol; and most preferred is octyldodecanol. Such preferred aliphatic fatty alcohols are particularly useful in combination with the volatile liquid silicone oils discussed herein to adjust the average solubility of the liquid base material.

c. Non-polar, Non-volatile Emollients

In addition to the liquids discussed above, the liquid base material can optionally include non-volatile, non-polar emollients which tend to improve product cosmetics. Typical non-volatile, non-polar emollients are disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989 get good dissolution. The non-volatile silicone oils useful in the present invention are essentially non-volatile polysiloxanes, paraffinic hydrocarbon oils, and mixtures thereof. The polysiloxanes useful in the present invention selected from the group consisting of polyalkylsiloxanes, polyarylsiloxanes, polyalkylarylsiloxanes, poly-ethersiloxane copolymers, and mixtures thereof. Examples of these include polydimethyl siloxanes having viscosities of from about 5 to about 100,000 centistokes at 25° C.

Among the preferred non-volatile silicone emollients useful in the present compositions are the polydimethyl siloxanes having viscosities from about 2 to about 400 centistokes at 25° C. Such polyalkylsiloxanes include the Viscasil® series (sold by General Electric Company) and the Dow Corning 200 series (sold by Dow Corning Corp.). Polyalkylarylsiloxanes include polymethylphenyl siloxanes having viscosities of from about 15 to about 65 centistokes at 25° C. These are available, for example, as SF 1075 methyl-phenyl fluid (sold by General Electric Company) and 556 Cosmetic Grade Fluid (sold by Dow Corning Corp.). Useful poly-ethersiloxane copolymers include, for example, a polyoxyalkylene ether copolymer having a viscosity of about 1200 to 1500 centistokes at 25° C. Such a fluid is available as SF1066 organosilicone surfactant (sold by General Electric Company). Polysiloxane ethylene glycol ether copolymers are preferred copolymers for use in the present compositions.

Non-volatile paraffinic hydrocarbon oils useful in the present invention include mineral oils and certain branched-chain hydrocarbons. Examples of these fluids are disclosed in U.S. Pat. No. 5,019,375 issued to Tanner et al. on May 28, 1991. Preferred mineral oils have the following properties:

(1) viscosity from about 5 centistokes to about 70 centistokes at 40° C.;

(2) density between about 0.82 and 0.89 g/cm$^3$ at 25° C.;

(3) flash point between about 138° C. and about 216° C.; and (4) carbon chain length between about 14 and about 40 carbon atoms.

Preferred branched chain hydrocarbon oils have the following properties:

(1) density between about 0.79 and about 0.89 g/cm$^3$ at 20° C.

(2) boiling point greater than about 250° C.; and (3) flash point between about 110° C. and about 200° C.

Particularly preferred branched-chain hydrocarbons include Permethyl 103A, which contains an average of about 24 carbon atoms; Permethyl 104A, which contains an average of about 68 carbon atoms; Permethyl 102A, which contains an average of about 20 carbon atoms; all of which may be purchased from Permethyl Corporation; and Ethylflo 364 which contains a mixture of 30 carbon atoms and 40 carbon atoms and may be purchased from Ethyl Corp.

Additional components useful in formulating these topical compositions are further described below.

IV. Additional Components

A wide variety of additional components can be employed in the hair care and topical skin compositions herein. Non-limiting examples include the following:

1. Deodorant Active Ingredients

Suitable types of deodorant actives include antimicrobial ingredients such as bactericides and fungicides. Exemplary deodorant actives include quaternary ammonium compounds such as cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichlorio-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Still other antimicrobial ingredients include farnesol.

Other deodorant actives include odor absorbing materials such as carbonate and bicarbonate salts, e.g. as the alkali metal carbonates and bicarbonates, ammonium and tetraalkylammonium carbonates and bicarbonates, especially the sodium and potassium salts.

Mixtures of deodorant actives are also contemplated and intended to be encompassed herein.

2. Antiperspirant Actives

The compositions of the present invention can also contain an astringent antiperspirant active. These actives are typically used at levels from about 0.5% to about 60%, preferably from about 5% to about 35%, in, e.g., an antiperspirant gel stick composition. This active can be incorporated either in solubilized or particulate form. These weight percentages are calculated on an anhydrous metal salt basis (exclusive of, e.g., glycine, the salts of glycine, or other complexing agents). Such materials include, for example, many aluminum or zirconium astringent salts or complexes and are well known in the antiperspirant art.

The antiperspirant active is preferably in particulate form wherein the surface area of the active is relatively low. The surface area of the antiperspirant active can be reduced by increasing the size and density of the active particles. Consequently, the particulate antiperspirant active preferably has a density which is preferably greater than about 0.7 g/cm$^3$ and an average particle size (as measured by a Coulter Multisizer 11 manufactured by Coulter Corporation, Haleah, Fla.) greater than about 10 microns; more preferably, greater than about 30 microns; and most preferably, greater than about 40 microns. Such preferred materials can be purchased from Westwood Chemical Company, Middletown, N.Y. under the trade name Westchlor® ZR. Suitable antiperspirant active is disclosed, for example in U.S. Pat. No. 4,147,766 which issued on Apr. 3, 1979 to Kozischek.

Any aluminum astringent antiperspirant salt or aluminum and/or zirconium astringent complex can be employed herein. Salts useful as astringent antiperspirant salts or as components of astringent complexes include aluminum halides, aluminum hydroxy-halides, zirconyl oxyhalides, zirconyl hydroxy-halides, and mixtures of these materials.

Aluminum salts of this type include aluminum chloride and the aluminum hydroxyhalides having the general formula $Al_2(OH)_xQ_y \cdot XH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. No. 3,887,692 issued to Gilman on Jun. 3, 1975, and U.S. Pat. No. 3,904,741 issued to Jones and Rubino on Sep. 9, 1975.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein z may vary from about 0.9 to about 2 and need not be an integer, n is the valence of B, 2-nz is greater than or equal to 0, and B may be selected from the group consisting of halides, nitrate, sulfamate, sulfate, and mixtures thereof. Although only zirconium compounds are exemplified in this specification, it will be understood that other Group IVB metal compounds, including hafnium, can be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than zero groups per molecule.

Several types of antiperspirant complexes utilizing the above antiperspirant salts are known in the art. For example, U.S. Pat. No. 3,792,068 issued to Luedders et al. on Feb. 12, 1974 discloses complexes of aluminum, zirconium and amino acids, such as glycine. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by (A) co-dissolving in water
 (1) one part $Al_2(OH)_{6-m}Q_m$, wherein Q is an anion selected from the group consisting of chloride, bromide and iodide, and m is a number from about 0.8 to about 2.0;
 (2) x parts $ZrO(OH)_{2-a}Q_a.nH_2O$, where Q is chloride, bromide or iodide; where a is from about 1 to about 2; where n is from about 1 to about 8; and where x has a value of from about 0.16 to about 1.2;
 (3) p parts neutral amino acid selected from the group consisting of glycine, dl-tryptophane, dl-b-phenylalanine, dl-valine, dl-methionine and b-alanine, and where p has a value of from about 0.06 to about 0.53;

(B) co-drying the resultant mixture to a friable solid; and (C) reducing the resultant dried inorganic-organic antiperspirant complex to particulate form.

A preferred aluminum compound for preparation of such ZAG type complexes is aluminum chlorhydroxide of the empirical formula $Al_2(OH)_5Cl.2H_2O$. Preferred zirconium compounds for preparation of such ZAG-type complexes are zirconyl hydroxychloride having the empirical formula $ZrO(OH)Cl.3H_2O$ and the zirconyl hydroxyhalides of the empirical formula $ZrO(OH)_{2-a}Cl_2.nH_2O$ wherein a is from about 1.5 to about 1.87, and n is from about 1 to about 7. The preferred amino acid for preparing such ZAG-type complexes is glycine of the formula $CH_2(NH_2)COOH$. Salts of such amino acids can also be employed in the antiperspirant complexes. See U.S. Pat. No. 4,017,599 issued to Rubino on Apr. 12, 1977.

A wide variety of other types of antiperspirant complexes are also known in the art. For example, U.S. Pat. No. 3,903,258 issued to Siegal on Sep. 2, 1975 discloses a zirconium aluminum complex prepared by reacting zirconyl chloride with aluminum hydroxide and aluminum chlorhydroxide. U.S. Pat. No. 3,979,510 issued to Rubino on Sep. 7, 1976 discloses an antiperspirant complex formed from certain aluminum compounds, certain zirconium compounds, and certain complex aluminum buffers. U.S. Pat. No. 3,981,896 issued to Pauling on Sep. 21, 1976 discloses an antiperspirant complex prepared from an aluminum polyol compound, a zirconium compound and an organic buffer. U.S. Pat. No. 3,970,748 issued to Mecca on Jul. 20, 1976 discloses an aluminum chlorhydroxy glycinate complex of the approximate general formula $[Al_2(OH)_4Cl][H_2CNH_2COOH]$.

Of all the above types of antiperspirant actives, preferred compounds include the 5/6 basic aluminum salts of the empirical formula $Al_2(OH)_5Cl.2H_2O$; mixtures of $AlCl_3.6H_2O$ and $Al_2(OH)_5Cl.2H_2O$ with aluminum chloride to aluminum hydroxychloride weight ratios of up to about 0.5; ZAG type complexes wherein the zirconium salt is $ZrO(OH)Cl.3H_2O$, the aluminum salt is $Al_2(OH)_5Cl.2H_2O$ or the aforementioned mixtures of $AlCl_3.6H_2O$ and $Al_2(OH)_5 Cl.2H_2O$ wherein the total metal to chloride molar ratio in the complex is less than about 1.25 and the Al:Zr molar ratio is about 3.3, and the amino acid is glycine; and ZAG-type complexes wherein the zirconium salt is $ZrO(OH)_{2-a}Cl_a.nH_2O$ wherein a is from about 1.5 to about 1.87 and n is from about 1 to about 7, the aluminum salt is $Al_2(OH)_5Cl.2H_2O$, and the amino acid is glycine.

Solubilized antiperspirant actives which can be utilized in the present invention are also well known in the art. These materials utilize monohydric or polyhydric alcohols or water to solublize the antiperspirant active before it is incorporated into the product. The levels of these polar solvents are typically less than about 25%, and preferably less than about 15% of the composition. Examples of such actives are taught, for example, in U.S. Pat. No. 4,137,306 issued to Rubino on Jan. 30, 1979; U.S. patent application Ser. No. 370,559, Smith and Ward, filed Jun. 23, 1989; and European Patent Application 0295070 which published Dec. 14, 1988, all of said patents and applications being incorporated herein by reference.

3. Pharmaceutical Actives

The compositions of the present invention, especially the topical skin care compositions, can comprise a safe and effective amount of a pharmaceutical active. The phrase "safe and effective amount", as used herein, means an amount of an active high enough to significantly or positively modify the condition to be treated, but low enough to avoid serious side effects (at a reasonable benefit/risk ratio), within the scope of sound medical judgement. A safe and effective amount of the pharmaceutical active will vary with the specific active, the ability of the composition to penetrate the active through the skin, the amount of composition to be applied, the particular condition being treated, the age and physical condition of the patient being treated, the severity of the condition, the duration of the treatment, the nature of concurrent therapy, and like factors.

The pharmaceutical actives which can be used in the compositions of the present invention preferably comprise from about 0.1% to about 20% by weight of the compositions, more preferably from about 0.1% to about 10%, and most preferably from about 0.1% to about 5%. Mixtures of pharmaceutical actives can also be used.

Nonlimiting examples of pharmaceutical actives useful in the compositions of the present invention include anti-acne drugs. Anti-acne drugs preferred for use in the present invention include the keratolytics such as salicylic acid, sulfur, lactic acid, glycolic, pyruvic acid, urea, resorcinol, and N-acetylcysteine; retinoids such as retinoic acid and its derivatives (e.g., cis and trans); antibiotics and antimicrobials such as benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate, and cholate. Preferred for use herein is salicylic acid.

Useful pharmaceutical actives in the compositions of the present invention include non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Useful pharmaceutical actives in the compositions of the present invention include antipruritic drugs. Antipruritic drugs preferred for inclusion in compositions of the present invention include pharmaceutically-acceptable salts of methdilizine and trimeprazine. Useful pharmaceutical actives in the compositions of the present invention include include anesthetic drugs. Anesthetic drugs preferred for inclusion in compositions of the present invention include pharmaceutically-acceptable salts of lidocaine, bupivacaine, chlorprocaine, dibucaine, etidocaine, mepivacaine, tetracaine, dyclonine, hexylcaine, procaine, cocaine, ketamine, pramoxine and phenol. Useful pharmaceutical actives in the compositions of the present invention include antimicrobial drugs (antibacterial, antifungal, antiprotozoal and antiviral drugs). Antimicrobial drugs preferred for inclusion in compositions of the present invention include pharmaceutically-acceptable salts of b-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, paromomycin, streptomycin, tobramycin, miconazole and amanfadine. Antimicrobial drugs preferred for inclusion in compositions of the present invention include tetracycline hydrochloride, erythromycin estolate, erythromycin stearate (salt), amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole.

4. Sunscreening Agents

Also useful herein are sunscreening agents. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Preferred among those sunscreens which are useful in the compositions of the instant invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.

Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens. Especially preferred examples of these sunscreens include those selected from the group consisting of 4-N,N-(2-ethylhexyl) methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl) methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See Federal Register, Vol. 43, No. 166, pp. 38206–38269, Aug. 25, 1978, which is incorporated herein by reference in its entirety.

5. Sunless tanning agents

Also useful in the present invention are sunless tanning agents including dihydroxyacetone, glyceraldehyde, indoles and their derivatives, and the like. These sunless tanning agents can also be used in combination with the sunscreen agents.

6. Conditioning Agents

Other useful actives include the conditioning agents disclosed hereinbefore, including hydrocarbons, silicone fluids, and cationic materials. The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof.

Silicone conditioning agents useful herein are the ones disclosed hereinbefore, especially those that have viscosities of less than about 5 centistokes at 25° C., while the cylic materials have viscosities of less than about 10 centistokes.

Cationic conditioning agents useful herein can include quaternary ammonium salts or the salts of fatty amines. Preferred quaternary ammonium salts are dialkyl dimethyl ammonium chlorides, wherein the alkyl groups have from 12 to 22 carbon atoms and are derived from long-chain fatty acids. Representative examples of quaternary ammonium salts include ditallow dimethyl ammonium chloride, ditallow dimethyl ammonium methyl sulfate, dihexadecyl dimethyl ammonium chloride, and di(hydrogenated tallow) ammonium chloride. Other qauternary ammonium salts useful herein are dicationics such as tallow propane diammonium dichloride. Quaternary imidazolinium salts are also useful herein. Examples of such materials are those imidazolinium salts containing $C_{12-22}$ alkyl groups such as 1-methyl-1-[(stearoylamide)ethyl]-2-heptadecyl-4,5-dihydroimidazolinium chloride, 1-methyl-1-[(palmitoylamide)ethyl]-2-octadecyl-4,5-dihydroimidazolinium chloride and 1-methyl-1-[(tallowamide)-ethyl]-2-tallow-imidazolinium methyl sulfate. Also useful herein are salts of fatty amines. Examples of such compounds include stearylamine hydrochloride, soyamine hydrochloride, and stearylamine formate. Useful conditioning agents are disclosed in U.S. Pat. No. 4,387,090, to Bolich, issued Jun. 7, 1983, which is incorporated by reference herein.

7. Humectants and Moisturizers

The compositions of the present invention can contain one or more humectant or moisturizing materials. A variety of these materials can be employed and each can be present at a level of from about 0.1% to about 20%, more preferably from about 1% to about 10% and most preferably from about 2% to about 5%. These materials include urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Preferred humectants and moisturizers are glycerol, butylene glycol, hexylene glycol, and mixtures thereof.

The compositions of the present invention, especially the conditioner compositions, can contain one or more surfactants as disclosed hereinbefore. These surfactants are useful adjuncts for the carriers of the present compositions. For conditioners, the preferred level of surfactant is from about 0.2% to about 3%. Surfactants useful in compositions of the present invention include anionic, nonionic, cationic, zwitterionic and amphoteric surfactants.

8. Carboxylic Acid Copolymer Thickeners

Another component useful in the compositions herein is a carboxylic copolymer thickener as disclosed hereinbefore. The non-rinsed compositions of the present invention can comprise from about 0.025% to about 1%, more preferably from about 0.05% to about 0.75% and most preferably from about 0.10% to about 0.50% of carboxylic acid polymer thickeners.

9. Emulsifiers

The non-rinsed compositions herein can contain various emulsifiers. These emulsifiers are useful for emulsifying the various carrier components of the compositions herein, and are not required for solubilizing or dispersing the copolymers of the present invention. Suitable emulsifiers can include any of a wide variety of nonionic, cationic, anionic, and zwitterionic emulsifiers disclosed in the prior patents and other references. See McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Suitable emulsfier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof. The emulsifiers can be used individually or as a mixture of two or more and can comprise from about 0.1% to about 10%, more preferably from about 1% to about 7%, and most preferably from about 1% to about 5% of the compositions of the present invention.

10. Emollients

The non-rinsed compositions useful in the methods of the present invention can also optionally comprise at least one emollient. Examples of suitable emollients include, but are not limited to, volatile and non-volatile silicone oils, highly branched hydrocarbons, and non-polar carboxylic acid and alcohol esters, and mixtures thereof. Emollients useful in the instant invention are further described in U.S. Pat. No. 4,919,934, to Deckner et al., issued Apr. 24 1990, which is incorporated herein by reference in its entirety.

The emollients can typically comprise in total from about 1% to about 50%, preferably from about 1% to about 25%, and more preferably from about 1% to about 10% by weight of the compositions useful in the present invention.

11. Additional Optional Components

A variety of additional components can be incorporated into the non-rinsed compositions herein. Non-limiting examples of these additional components include vitamins and derivatives thereof (e.g., ascorbic acid, vitamin E, tocopheryl acetate, retinoic acid, retinol, retinoids, and the like); low pH thickening agents (e.g. polyacrylamide and $C_{13-14}$ isoparaffin and laureth-7, available as Sepigel from Seppic Corporation; polyquaternium and mineral oil, available as Salcare SC92, from Allied Colloids; crosslinked methyl quaternized dimethylaminomethacrylate and mineral oil, available as Salcare SC95 from Allied Colloids; resins; gums and thickeners such as xanthan gum, carboxymethyl cellulose, hydroxymethyl cellulose, hydroxyethyl cellulose, alkyl-modified hydroxyalkyl celluloses (e.g. long chain alkyl modified hydroxyethyl celluloses such as cetyl hydroxyethylcellulose), and magnesium aluminum silicate; cationic polymers and thickeners (e.g., cationic guar gum derivatives such as guar hydroxypropyltrimonium chloride and hydroxypropyl guar hydroxypropyltrimonium chloride, available as the Jaguar C series from Rhone-Poulenc; polymers for aiding the film-forming properties and substantivity of the composition (such as a copolymer of eicosene and vinyl pyrrolidone, an example of which is available from GAF Chemical Corporation as Ganex® (V-220); suspending agents such as ethylene glycol distearate and the like; preservatives for maintaining the antimicrobial integrity of the compositions; skin penetration aids such as dimethylsulfoxide (DMSO), 1-dodecylazacycloheptan-2-one (available as Azone from the Upjohn Co.) and the like; antioxidants; chelators and sequestrants; and aesthetic components such as fragrances, colorings, essential oils, skin sensates, astringents, skin soothing agents, skin healing agents and the like, nonlimiting examples of these aesthetic components include panthenol and derivatives (e.g. ethyl panthenol), pantothenic acid and its derivatives, clove oil, menthol, camphor, eucalyptus oil, eugenol, menthyl lactate, witch hazel distillate, allantoin, bisabalol, dipotassium glycyrrhizinate and the like. Other useful actives include skin bleaching (or lightening) agents including but not limited to hydroquinone, ascorbic acid, kojic acid and sodium metabisulfite. Actives which are especially useful for hair care compositions include anti-dandruff actives such as zinc pyrithione, octopirox, selenium disulfide, sulfur, coal tar, and the like, and hair curling and/or straightening actives as are well known in the art.

Method of Using Non-Rinsed Hair and Skin Care Compositions

The hair care and skin care compositions of the present invention are used in conventional ways to provide the desired benefit appropriate to the product such as hair styling, holding, cleansing, conditioning and the like for hair care compositions and benefits such as moisturization, sun protection, anti-acne, anti-wrinkling, artificial tanning, analgesic, and other cosmetic and pharmaceutical benefits for skin care compositions. Such methods of use depend upon the type of composition employed but generally involve application of an effective amount of the product to the hair or skin, which can then be allowed to remain on the hair (as in the case of spray, mousse, or gel products), or allowed to remain on the skin (as in the case of the skin care compositions). By "effective amount" is meant an amount sufficient to provide the benefit desired. Preferably, mousse, and gel products are applied to wet or damp hair prior to drying and styling of the hair. After such compositions are applied to the hair, the hair is dried and styled in the usual ways of the user. Hair sprays are typically applied to dry hair after it has already been dried and styled. Cosmetic and pharmaceutical topical skin care compositions are applied to and rubbed into the skin.

The following examples further illustrate preferred embodiments within the scope of the present invention. The examples are given solely for the purposes of illustration and are not to be construed as limitations of the present invention as many variations of the invention are possible without departing from its spirit and scope.

EXAMPLES

The following Examples further describe and demonstrate the preferred embodiments within the scope of the present invention. The Examples are given solely for the purpose of illustration and are not to be construed as limitations of the present invention as many variations thereof are possible without departing from its spirit and scope. All percentages, ratios, and parts herein, in the Specification, Examples, and Claims, are by weight and are approximations, unless otherwise stated.

Five different perfume compositions are used in the following examples. Perfume A and B are examples of enduring perfume compositions of this invention. Comparative Perfumes C, D, and F are non-enduring perfume compositions which are outside the scope of this invention.

| Perfume A | | | |
|---|---|---|---|
| Perfume Ingredients | Approximate B.P. (°C.) | ClogP | Wt. % |
| Benzyl salicylate | 300 | 4.383 | 20 |
| Ethylene brassylate | 332 | 4.554 | 20 |
| Galaxolide - 50%[a] | +300 | 5.482 | 20 |
| Hexyl cinnamic aldehyde | 305 | 5.473 | 20 |
| Tetrahydro linalool | 191 | 3.517 | 20 |
| | | | Total 100 |

[a] A 50% solution in benzyl bonzoate. Perfume A contains about 80% of enduring perfume components having BP > 250° C. and ClogP > 3.0.

| Perfume B | | | |
|---|---|---|---|
| Perfume Ingredients | Approximate B.P. (°C.) | ClogP | Wt. % |
| Benzyl acetate | 215 | 1.960 | 4 |
| Benzyl salicylate | 300 | 4.383 | 12 |
| Coumarin | 291 | 1.412 | 4 |
| Ethylene brassylate | 332 | 4.554 | 10 |
| Galaxolide - 50%[a] | +300 | 5.482 | 10 |
| Hexyl cinnamic aldehyde | 305 | 4.853 | 20 |
| Lilial | 258 | 3.858 | 15 |
| Methyl dihydro isojasmonate | +300 | 3.009 | 5 |
| gamma-n-Methyl ionone | 252 | 4.309 | 10 |
| Patchouli alcohol | 283 | 4.530 | 4 |
| Tetrahydro linalool | 191 | 3.517 | 6 |
| | | | Total 100 |

[a] used as a 50% solution in isopropyl myristate which is not counted in the composition. Perfume B contains about 86% of enduring perfume components having BP > 250° C. and ClogP > 3.0.

| Comparative Perfume C | | | |
|---|---|---|---|
| Perfume Ingredients | Approximate B.P. (°C.) | ClogP | Wt. % |
| Benzyl acetate | 215 | 1.960 | 20 |
| laevo-Carvone | 231 | 2.083 | 20 |
| Dihydro myrcenol | 208 | 3.030 | 20 |
| Hydroxycitronellal | 241 | 1.541 | 20 |
| Phenyl ethyl alcohol | 220 | 1.183 | 20 |
| | | | Total 100 |

Comparative Perfume C contains about 80% of non-enduring perfume ingredients having BP<250° C. and ClogP<3.0.

| Comparative Perfume D | | | |
|---|---|---|---|
| Perfume Ingredients | Approximate B.P. (°C.) | ClogP | Wt. % |
| Eugenol | 253 | 2.307 | 20 |
| iso-Eugenol | 266 | 2.547 | 20 |
| Fenchyl alcohol | 200 | 2.579 | 20 |
| Methyl dihydrojasmonate | +300 | 2.319 | 20 |
| Vanillin | 285 | 1.580 | 20 |
| | | | Total 100 |

Comparative Perfume D contains about 80% of non-enduring perfume ingredients having BP>250° C. and ClogP<3.0.

Comparative Perfume E

| Perfume Ingredients | Approximate B.P. (°C.) | ClogP | Wt. % |
|---|---|---|---|
| Iso-Bornyl acetate | 227 | 3.485 | 20 |
| para-Cymene | 179 | 4.068 | 20 |
| d-Limonene | 177 | 4.232 | 20 |
| gamma-n-Methyl ionone | 252 | 4.309 | 20 |
| Tetrahydromyrcenol | 200 | 3.517 | 20 |
| | | Total | 100 |

Comparative Perfume E contains about 80% of non-enduring perfume ingredients having BP<250° C. and ClogP>3.0.

Examples 1–10
(Shampoo Compositions)

The following examples exemplify shampoo compositions of the present invention.

The compositions of the present invention, in general, can be made by mixing the materials together at elevated temperature, e.g., about 72° C. The silicone resin, if any, and silicone fluid component are first mixed together before being mixed with the other ingredients. The other ingredients are added and the complete mixture is mixed thoroughly at the elevated temperature and is then pumped through a high shear mill and then through a heat exchanger to cool it to ambient temperature. The average particle size of the silicone is preferably from about 0.5 to about 20 microns. Also alternately, a portion of the liquid components or soluble components (including, for example, cationic polymer conditioning agent) can be added to the composition after cooling the mix of surfactants and solids; if no insoluble ingredients exist, all ingredients can be combined at ambient temperature.

Alternately, the silicone conditioning agent can be processed by:

(1) mixing with anionic surfactant and fatty alcohol, such as cetyl and stearyl alcohols at elevated temperature, to form a premix containing dispersed silicone. The premix can then be added to and mixed with the remaining materials of the shampoo, pumped thorough a high shear mill, and cooled; or (2) adding silicone, ammonium laureth-3 sulfate and ammonium chloride to a high shear mixing vessel and mixing for about 30 minutes or until the desired silicone particle size is achieved. Levels of the three ingredients and time of mixing will very depending of type of oil to be emulsified.

The compositions of the Examples 1–10 provide excellent in-use hair cleaning, lather, mildness, conditioning (where applicable), and especially long lasting perfume benefit even after the hair is dried with an electric hair dryer.

TABLE

Ingredients (ppm or %, by weight, of composition)

| | Compositions | | | | |
|---|---|---|---|---|---|
| | 1 | 2 | 3 | 4 | 5 |
| Sodium Laureth-3 Sulfate | 13.50 | 13.5 | 16.0 | 8.0 | 16.0 |
| Ammonium Lauryl Sulfate | 4.5 | 4.5 | 1.5 | 8.0 | 3.0 |
| Sodium Lauryl Sarcosinate[6] | — | — | 3.75 | 0.5 | — |
| Coconut Monoethanol Amide | 2.5 | 1.0 | — | — | 1.0 |
| Polyquaternium 10[1] | 0.025 | 0.025 | — | — | 0.05 |
| Ethylene Glycol Distearate | 1.5 | 1.5 | 2.0 | 3.0 | 2.5 |
| Dimethicone[2] | — | 0.5 | 1.0 | 2.5 | — |
| Cetyl Alcohol | — | — | — | 0.4 | — |
| Stearyl Alcohol | — | — | — | 0.2 | — |
| Propylene Glycol | 1.0 | — | — | — | — |
| Light Mineral Oil | 0.5 | — | 0.5 | — | — |
| Isopropyl Isostearate | — | 0.5 | 0.5 | — | 1.5 |
| Glycerine | 1.0 | — | — | — | — |
| Perfume A | 0.65 | 0.65 | — | — | — |
| Perfume B | — | — | 0.40 | 0.50 | 0.25 |
| DMDM Hydantoin | 0.20 | 0.20 | 0.30 | 0.30 | 0.30 |
| PEG 600[4] | 0.125 | 0.125 | — | — | — |
| Sodium Sulfate | 0.50 | 0.25 | — | — | 1.0 |
| Tricetylmethylammonium chloride[7] | — | 0.15 | 0.55 | — | — |
| Color Solution (ppm) | 10 | 10 | 20 | 20 | 20 |
| Sodium Chloride | Add as needed to thicken to target viscosity | | | | |
| Ammonium Xylene Sulfonate[3] | Add as needed to thicken to target viscosity | | | | |
| Water | q.s. to 100% | | | | |

| | Compositions | | | | |
|---|---|---|---|---|---|
| | 6 | 7 | 8 | 9 | 10 |
| Sodium Laureth-3 Sulfate | 13.5 | 13.5 | 16.0 | 8.0 | 16.0 |
| Ammonium Lauryl Sulfate | 4.5 | — | — | 8.0 | 3.0 |
| Cocoamidopropyl Betaine[5] | — | 5.0 | 3.75 | 0.5 | — |
| Coconut Monoethanol Amide | 2.5 | 1.0 | — | — | 1.0 |
| Polyquaternium 10[1] | 0.025 | 0.025 | — | — | 1.0 |
| Dimethicone Copolyol | — | 1.5 | 1.0 | — | — |
| Propylene Glycol | 1.0 | — | — | — | — |
| Glycerine | 1.0 | — | — | — | — |
| Perfume B | 0.65 | 0.65 | 0.40 | 0.50 | 0.25 |
| DMDM Hydantoin | 0.20 | 0.20 | 0.30 | 0.30 | 0.30 |
| Sodium Sulfate | 0.50 | 0.25 | — | — | 1.0 |
| Color Solution (ppm) | 10 | 10 | 20 | 20 | 20 |
| Sodium Chloride | Add as needed to thicken to target viscosity | | | | |
| Ammonium Xylene Sulfonate[3] | Add as needed to thicken to target viscosity | | | | |
| Water | q.s. to 100% | | | | |

[1]Ucare ® Polymer JR-30M, commercially available from Union Carbide Corporation.
[2]A 40/60 blend of SE-76 silicone gum. available from GE Sili cones and a silicone fluid having a viscosity of about 350 centistokes.
[3]Commercially available as a 40% solution and used to thin product to target viscosity.
[4]Commercially available as a 100% active fluid.
[5]Available under the tradename Genagen ® CAB from Hoechst Celanese as a 30% active solution.
[6]Available under the tradename Hamposyl ® L-30 from Hampshire Chemical Corp. as a 30% active solution.
[7]"TCMAC" available commercially from Akzo-Chemie as Arquad ®-316 as a 90% suspension.

Comparative Examples 11–13

Shampoo Compositions of the Comparative Examples 11–13 are made similarly to that of Example 1, except that the non-enduring perfumes C, D, and E respectively, are used instead of Perfume A. Hair worked with shampoo composition of the Comperative Examples 11–13 has noticeably less perfume odor and less long lasting perfume odor especially after the drying step with an electric hair dryer, than when the shampoo composition of Example 1 is used.

Examples 14 to 21
(Foaming shower products)

The following are personal cleansing compositions in the form of foaming shower products and which are representative of the present invention:

| Component | Compositions | | | | |
|---|---|---|---|---|---|
| | 14 | 15 | 16 | 17 | 18 |
| Amphoteric[1] | 7.5 | 3.0 | 5.0 | 5.0 | 2.5 |
| Sodium N-lauryl-beta-amino propionate | — | 5.0 | 3.0 | — | 5.0 |
| Sodium laureth-3 sulfate | 7.5 | 9.0 | 10.0 | 10.0 | 7.5 |
| APG[2] | 2.5 | — | 2.0 | 2.0 | — |
| Coconut diethanolamide | 3.0 | 1.0 | — | 2.0 | 1.0 |
| Cocoamidopropyldimethyl-carboxymethyl betaine | — | 2.0 | 2.0 | 1.0 | 2.5 |
| Ceraphyl GA[3] | 5.0 | 4.0 | 6.0 | 6.0 | 5.0 |
| Polymer 1[4] | — | 0.1 | 0.2 | — | 0.1 |
| Polymer 2[5] | 0.2 | 0.1 | — | 0.2 | 0.1 |
| Myristic acid | 4.0 | 2.0 | 1.5 | 1.0 | 2.0 |
| Preservative | 0.15 | 0.15 | 0.15 | 0.15 | 0.15 |
| Pearlescer | 0.5 | — | — | 1.0 | 1.0 |
| Perfume A | 0.7 | 0.7 | 0.7 | 0.7 | 0.7 |
| Water | | | to 100 | | |

| Ingredients | Compositions | | |
|---|---|---|---|
| | 19 | 20 | 21 |
| Amphoteric[1] | 5.0 | 5.0 | — |
| Sodium laureth-3 sulfate | 10.0 | 10.0 | — |
| APG[2] | 2.5 | 2.5 | — |
| Coconut diethanolamide | 3.0 | — | — |
| Coconut monoethanolamide | — | 3.0 | 2.82 |
| Cocoamidopropyldimethyl-carboxymethyl betaine | 2.5 | — | — |
| Ceraphyl GA[3] | 5.0 | 5.0 | — |
| Polymer 1[4] | 0.2 | — | — |
| Polymer 2[5] | — | 0.2 | — |
| PEG[6] caprylic/capric glyceride | 2.0 | 1.0 | 4.0 |
| Myristic acid | 2.0 | 2.0 | 2.0 |
| Maleated soybean oil | — | — | 2.0 |
| Soybean oil | 5.0 | 5.0 | 8.0 |
| Preservative | 0.2 | 0.2 | — |
| Pearlescer | 2.0 | 1.0 | — |
| Perfume B | 1.0 | 1.0 | 1.70 |
| Na/Mg laureth-3–3.6 sulfate | — | — | 12.0 |
| Sodium lauryl amphoacetate | — | — | 6.0 |
| Decylglucoside | — | — | 2.5 |
| Polyquaternium-10 (JR-30M) | — | — | 0.40 |
| Glycerine | — | 3.0 | 3.0 |
| Titanium dioxide | — | — | 0.10 |
| Sodium benzoate | — | — | 0.25 |
| Glydant | — | — | 0.13 |
| Sodium EDTA | — | — | 0.13 |
| Mg sulfate heptahydrate | — | — | 0.55 |
| Water | | to 100 | |

[1]Empigen ® CDR 60 — an aqueous mixture of about 26.5% cocoamphoacetate (the amphoteric of Formula I and/or IV in which $R_1$ is coconut alkyl, $R_2$ is H, and Z is $CO_2Na$) and about 1.5% cocoamphodiacetate (the amphoteric of Formula I and/or IV in which $R_1$ is coconut alkyl, $R_2$ is $CH_2CO_2Na$, and Z is $CO_2Na$).
[2]Alkylpolysaccharide of Formula VI in which R is $C_8$–$C_{10}$ alkyl, t is 0, Z is a glycose residue, and x is about 1.5.
[3]Maleated soybean oil marketed by Van Dyke.
[4]Merquat ® 550 — copolymer of acrylamide and dimethyldiallyl ammoniumchloride, mol. wt. 2.5 × $10^6$ (8% solution).
[5]Polymer JR-400 ® — hydroxyethylcellulose reacted with epichlorohydrin and quaternized with trimethylamine, mol. wt. 4 × $10^6$.

Compositions 14 to 18 are prepared by: forming a gel phase A of Merquat 550 and/or JR-400 in water; forming an aqueous phase B containing the remaining water-soluble, oil-insoluble ingredients; forming an oil phase C containing the Ceraphyl GA, myristic acid, coconut diethanolamide, and pearlescer; admixing phases A and B and heating to about 65°–70° C.; heating phase C to about 65°–70° C. and admixing with mix of phases A and B; cooling to about 40°–45° C.; adding preservative, and cooling to ambient temperature and adding the perfume A. Compositions 19 to 21 are prepared by: forming a surfactant phase A containing a portion of the water, the anionic and amphoteric surfactants and the remaining water-soluble, oil-insoluble ingredients; forming an oil phase B containing the myristic acid, coconut diethanolamide, PEG(6) caprylic/capryl glycerate and oil; admixing B with A at about 40°–50° C.; adding the remaining water, preservative and perfume B; cooling to ambient temperature; and admixing the Ceraphyl GA. The average particle size of the emulsion droplets is about 30 micron (Malvern Series 2600 laser diffraction).

The products provide excellent in-use and efficacy benefits including cleansing and lathering together with improved mildness and skin conditioning (hydration, suppleness, etc.), and especially long lasting perfume benefit.

Comparative Examples 22–24

Foaming shower compositions of Comparative Examples 22–24 are made similar to that of Example 19, except that the non-enduring Perfumes C, D and E, respectively, are used instead of Perfume B. The compositions of Comparative Examples 22–24 provide less noticeable perfume odor benefit and the perfume odor is significantly less long lasting, as compared to the composition of Example 19.

Examples 25 to 34
(Personal Cleansing Compositions Containing Soap)

| Ingredients | Compositions | | | | |
|---|---|---|---|---|---|
| | 25 | 26 | 27 | 28 | 29 |
| 1) Soap (K or Na) 30% Laurate 30% Myristate 25% Palmitate 15% Stearate | 15.00 | 11.00 | 11.00 | 8.00 | 1.00 |
| 2) Fatty acids (above ratios) | 4.50 | 1.50 | 1.50 | 0.50 | 0.50 |
| 3) Na Lauryl Sarcosinate | 6.00 | 6.00 | 6.00 | 6.00 | 6.00 |
| 4) Sodium Laureth-3 Sulfate | 0.66 | 0.66 | 0.66 | 0.66 | 0.66 |
| 5) Cocamidopropyl-betaine | 1.33 | 1.33 | 1.33 | 1.33 | 1.33 |
| 6) Glycerine | 15.00 | 15.00 | 15.00 | 15.00 | 15.00 |
| 7) Propylene glycol | 9.00 | 9.00 | 9.00 | 9.00 | 9.00 |
| 8) Polyquaternium 10 | 0.80 | 0.80 | 0.80 | 0.80 | 0.80 |
| 9) Ethylene glycol distearate (EDTA) | 1.50 | 1.50 | 1.50 | 1.50 | 1.50 |
| 10) Propylparaben | 0.10 | 0.10 | 0.10 | 0.10 | 0.10 |
| 11) Methylparaben | 0.20 | 0.20 | 0.20 | 0.20 | 0.20 |
| 12) Perfume A | 1.00 | 1.00 | — | — | — |
| 13) Perfume B | — | — | 1.00 | 1.00 | 1.00 |
| 14) KOH or NaOH | If necessary, adjust premix to pH = 7 | | | | |
| 15) Water | Balance to 100 | | | | |

| | Compositions | | | | |
|---|---|---|---|---|---|
| | 30 | 31 | 32 | 33 | 34 |
| 1) Soap (K or Na) 30% Laurate | 20.00 | 25.00 | 15.00 | 15.00 | 11.00 |

-continued

| Ingredients | | | | | |
|---|---|---|---|---|---|
| 30% Myristate 25% Palmitate 15% Stearate | | | | | |
| 2) Fatty acids (above ratios) | 1.5 | 1.0 | 1.50 | 1.50 | 1.50 |
| 3) Na Lauryl Sarcosinate | 6.00 | — | 6.00 | 6.00 | 6.00 |
| 4) Sodium Laureth-3 Sulfate | 0.66 | — | 0.66 | 0.66 | 0.66 |
| 5) Cocamidopropyl betaine | — | — | 1.33 | 1.33 | 1.33 |
| 6) Glycerine | — | 10.00 | 15.00 | — | 15.00 |
| 7) Propylene glycol | 9.00 | 9.00 | 9.00 | 15.00 | — |
| 8) Polyquaternium 10 | — | — | 0.80 | 0.80 | 0.80 |
| 9) Ethylene glycol distearate (EDTA) | — | — | 1.50 | 1.50 | 1.50 |
| 10) Propylparaben | 0.10 | 0.10 | 0.10 | 0.10 | 0.10 |
| 11) Methylparaben | 0.20 | 0.20 | 0.20 | 0.20 | 0.20 |
| 12) Perfume B | 1.10 | 1.10 | 1.10 | 1.10 | 1.10 |
| 13) KOH or NaOH | If necessary, adjust premix to pH = 7 | | | | |
| 14) Water | Balance to 100 | | | | |

Compositions 25 through 34 were prepared as follows:

1. Adding the fatty acids to the mixing vessel and begin heating to about 150° F. to 160° F.;
2. Adding the propylene glycol to the mixing vessel, continue heating and mixing;
3. In a separate mixing vessel, mixing the Polyquaternium 10 polymer into the glycerin (polymer premix), until the polymer hydrates (approximately 10 minutes);
4. When the fatty acids are completely melted, reacting the fatty acid mixture to soap with KOH (45% solution) and the water;
5. After reaction is completed, adding the following ingredients one at a time, ensuring complete mixing between each and maintaining a batch temperature of about 150° F. to 160° F.):
   a) Polymer premix
   b) Ethylene glycol distearate
   c) Methyl and propylparaben
   d) Sodium lauroyl sarcosinate
   e) Cocamidopropyl betaine
   f) Sodium laureth-3 sulfate
6. Flash cooling the batch to about 90° F. to 95° F. then adding and thoroughly mixing in the following materials:
   a) Phenoxyethanol
   b) Perfume

Examples 35 to 43
(Personal Cleansing Emulsion Compositions without Soap)

The following oil-in-water emulsions contain no soap, have an average oil droplet size of about 30 microns, and have a pH from about 4.5 to about 7.5.

| Ingredients | Compositions | | | | |
|---|---|---|---|---|---|
| | 35 | 36 | 37 | 38 | 34 |
| Na Mg Laureth-3.6 sulfate | 12.00 | 12.00 | 12.00 | 12.00 | 12.00 |
| Lauroamphoacetate | 6.00 | 6.00 | 6.00 | 6.00 | 6.00 |
| Decylglucoside | 2.50 | 2.50 | 2.50 | 2.50 | 2.50 |
| Cocamide MEA | 2.82 | 2.82 | 2.82 | — | 2.82 |
| Soybean oil | 8.00 | 8.00 | 8.00 | 8.00 | 8.00 |
| PEG-6 caprylic/ capric glycerides | 4.00 | 4.00 | 4.00 | 4.00 | 4.00 |
| Glycerine | 3.00 | 3.00 | 3.00 | 3.00 | 3.00 |
| Maleated soybean oil | 2.00 | 2.00 | 2.00 | 2.00 | 2.00 |
| Myristic acid | 1.60 | 1.60 | 1.60 | 1.60 | 1.60 |
| Citric acid | 1.40 | 1.40 | 1.40 | 1.40 | 1.40 |
| Polyquaternium 10 | 0.40 | 0.40 | 0.40 | 0.40 | — |
| Sodium benzoate | 0.25 | 0.25 | 0.25 | 0.25 | 0.25 |
| Glydant | 0.14 | 0.14 | 0.14 | 0.14 | 0.14 |
| Disodium EDTA | 0.13 | 0.13 | 0.13 | 0.13 | 0.13 |
| Titanium dioxide | 0.10 | 0.10 | 0.10 | 0.10 | 0.10 |
| Mg Sulfate heptahydrate | 0.10 | 0.10 | 0.10 | 0.10 | 0.10 |
| Perfume A | 1.00 | 1.00 | 1.00 | 1.00 | 1.00 |
| Water | Balance to 100 | | | | |

| | Compositions | | | |
|---|---|---|---|---|
| | 40 | 41 | 42 | 43 |
| Na Mg Laureth-3.6 sulfate | 12.00 | 15.00 | — | — |
| Lauroamphoacetate | — | 6.00 | 10.00 | 8.00 |
| Decylglucoside | 2.50 | — | 2.50 | 2.50 |
| Cocamide MEA | — | — | 2.82 | 2.802 |
| Soybean oil | 8.00 | 8.00 | 8.00 | 8.00 |
| PEG-6 caprylic/ capric glycerides | 4.00 | 4.00 | 4.00 | 4.00 |
| Glycerine | 3.00 | 3.00 | 3.00 | 3.00 |
| Maleated soybean oil | 2.00 | 2.00 | 2.00 | 2.00 |
| Myristic acid | 1.60 | — | 1.60 | 1.60 |
| Citric acid | 1.40 | 1.40 | 1.40 | 1.40 |
| Polyquaternium 10 | 0.40 | 0.40 | 0.40 | 0.40 |
| Sodium benzoate | 0.25 | 0.25 | 0.25 | 0.25 |
| Glydant | 0.14 | 0.14 | 0.14 | 0.14 |
| Disodium EDTA | 0.13 | 0.13 | 0.13 | 0.13 |
| Titanium dioxide | 0.10 | 0.10 | 0.10 | 0.10 |
| Mg Sulfate heptahydrate | 0.10 | 0.10 | 0.10 | 0.10 |
| Perfume B | 1.20 | 1.20 | 1.20 | 1.20 |
| Water | Balance to 100 | | | |

Compositions 35 to 43 are prepared by: forming a gel phase A by dispersing Polyquaternium 10 in water at about 25° C. with strong agitation. When phase A is thoroughly dispersed begin heating to about 45°–50° C. and add decylglucoside and lauroamphoacetate while mixing. Then add sodium magnesium laureth-3.6 sulfate. Add sodium benzoate, disodium EDTA, citric acid, and titanium dioxide while heating to about 60°–65° C. and mix until homogeneous.

Prepare phase B by mixing per-6 carpylic/capric glycerides, cocamide MEA, and myristic acid together at about 60°–65° C. When solids have melted, add soybean oil.

Add phase B to phase A and mix until emulsified, then start cooling.

Adjust pH if necessary with citric acid.

At about 45°–50° C. add glycerine. At about 40°–45° C. add DMDM Hydantoin, maleated soybean oil, magnesium sulfate heptahydrate, and perfume. Cool to ambient temperature.

Examples 44 to 54

The following examples are liquid hand washing compositions containing enduring perfume compositions.

| Ingredients | Compositions | |
|---|---|---|
| | 44 | 45 |
| Sodium lauryl sulfate | 6.00 | 3.80 |
| Sodium laureth-3 sulfate | 4.00 | 7.60 |
| Cocamidopropyl betaine | 1.20 | 1.35 |
| Lauramide DEA | 2.86 | 2.50 |
| Sodium sulfate | 0.45 | 2.10 |
| Tetrasodium EDTA | 0.10 | 0.10 |
| Glydant | 0.20 | 0.20 |
| Citric acid | 0.20 | 0.25 |
| Ethylene glycol distearate | 1.50 | — |
| Pearlescer | — | 0.43 |
| Polymer Jaguar C-14S | 0.25 | — |
| Perfume A | 0.25 | — |
| Perfume B | — | 0.30 |
| Water | Balance to 100 | |

| | Compositions | | | | |
|---|---|---|---|---|---|
| | 46 | 47 | 48 | 49 | 50 |
| Myristic acid | — | — | 7.51 | 1.50 | — |
| Tallow fatty acid | — | — | 6.51 | — | — |
| Potassium hydroxide | — | — | 2.90 | 3.36 | — |
| Mono sodium lauryl phosphate | — | — | — | 13.33 | — |
| Ammonium or sodium laureth-3 sulfate | 6.00 | 6.00 | 2.00 | — | — |
| Cocoamphodiacetate | 3.00 | 3.00 | 2.00 | 2.0 | — |
| Decylglucoside | — | — | — | — | 3.0 |
| Lauramine oxide | — | — | — | — | 10.0 |
| Glucose amide | 2.71 | 2.70 | — | — | 2.70 |
| Na Lauryl sarcosinate | — | 1.50 | — | 2.0 | — |
| Cocamidopropyl betaine | — | 3.75 | 2.00 | 2.0 | — |
| Soybean oil | — | — | 4.00 | — | — |
| Caprylic/capric glycerides | — | — | 2.50 | 2.50 | — |
| Glycerine | 5.00 | — | — | — | — |
| Dimethicone copolyol (Dow 193) | 2.00 | — | — | — | — |
| Zinc stearate | — | 0.80 | — | — | — |
| Cetyl alcohol | — | 1.00 | 1.00 | 1.50 | 1.50 |
| Carbomer | — | 0.40 | — | 1.50 | — |
| EGDS | — | 1.00 | 1.00 | — | — |
| Polyquaternium 10 | 1.00 | — | 0.80 | 0.40 | — |
| Polyquaternium 11 | — | 0.80 | — | — | — |
| Perfume A | 0.90 | 0.90 | 0.90 | 0.90 | 0.80 |
| Sodium benzoate | 0.25 | 0.25 | 0.25 | 0.25 | 0.25 |
| Disodium EDTA | 0.13 | 0.13 | 0.13 | 0.13 | 0.13 |
| DMDM Hydantoin | 0.14 | 0.14 | 0.14 | 0.14 | 0.14 |
| Water | Balance to 100 | | | | |

| | Compositions | | | |
|---|---|---|---|---|
| | 51 | 52 | 53 | 54 |
| Ammonium or sodium laureth-3 sulfate | 12.00 | 5.00 | — | — |
| Cocamidopropyl amine oxide | — | 5.00 | 2.50 | 2.00 |
| Na Lauryl sarcosinate | 3.00 | — | — | — |
| Sodium cocoyl isethionate | — | 5.00 | — | 10.00 |
| Cocamidopropyl betaine | — | — | — | 2.0 |
| Glycerine | — | — | 10.00 | — |
| Propylene glycol | — | — | — | 9.00 |
| Sodium benzoate | 0.25 | 0.25 | 0.25 | 0.25 |
| Disodium EDTA | 0.13 | 0.13 | 0.13 | 0.13 |
| DMDM Hydantoin | 0.14 | 0.14 | 0.14 | 0.14 |
| Perfume B | 0.90 | 0.80 | 0.80 | 0.80 |
| Water | Balance to 100 | | | |

Compositions 44 to 54 are prepared by: forming a gel phase A comprising water and polymer (e.g., Carbomer, Polyquaternium 10, Polyquaternium 11). When phase A is completely dispersed, begin heating to about 70° C. Add all additional ingredients except preservatives (DMDM Hydantoin, disodium EDTA, and sodium benzoate) and fragrance. Cool to about 30° C. and add fragrance, and preservatives. Cool to ambient temperature while mixing.

Examples 55–58

Hair Spray

Hair spray compositions are prepared from the following components utilizing conventional mixing techniques.

| | Compositions | | | |
|---|---|---|---|---|
| Ingredients | 55 | 56 | 57 | 58 |
| Water | QS 100 | QS 100 | QS 100 | QS 100 |
| Ethanol (SCA 40) | 79.0 | 79.0 | 79.0 | 90.0 |
| Copolymer[1] | 4.0 | 4.0 | 3.0 | 3.0 |
| Perfume B | 0.1 | 0.2 | 0.3 | 0.4 |

[1] Poly(n-butyl-co-2-methoxyethalacrylate)-graft-poly(2-ethyl-2-oxazoline) thermoplastic elastomeric copolymer, prepared by the following method.

To a 500 mL round-bottomed flask is added about 20.8 g (about 0.1623 mol) of n-butyl acrylate, about 11.2 g (about 0.0861 mol) of 2-methoxyethyl acrylate, about 0.30 g (about 0.002 mol) p-vinylbenzyl chloride, and about 0.02 g (about 0.0012 mol) of azoisobutyronitrile (AIBN) initator, in about 200 mL of acetone. The resulting solution is refluxed slowly for about 24 hours. The reaction is then quenched by the addition of about 5 mL of methanol and cooled to room temperature. The solvents are removed by rotary evaporation and the resulting polymer is dissolved in about 250 mL of dry acetonitrile. Next, about 20.0 g (about 0.2018 mol) of 2-ethyl-2-oxazoline and about 0.44 g (about 0.0029 mol) of sodium iodide is added and the solution is heated to about 90° C. for about 20 hours. The resulting solution is filtered and the solvent is evaporated to yield about 45.0 g (about 86% yield) of the thermoplastic elastomeric copolymer.

Preparation of Compositions 55–58

These products are prepared by first dissolving the polymer in the ethanol with stirring. The water and fragrance are then added with stirring. The resulting hair spray compositions can then be packaged in a nonaerosol spray pump. Alternatively, the compositions can be combined with conventional propellants and packaged in an aerosol spray.

These hair sprays are useful for application to the hair to provide a styling and holding benefit.

Examples 59–62

Reduced Volatile Organic Content Hairspray

Hair spray compositions are prepared from the following components utilizing conventional mixing techniques.

| Ingredients | 59 | 60 | 61 | 62 |
|---|---|---|---|---|
| Water | QS 100 | QS 100 | QS 100 | QS 100 |
| Ethanol | 54.0 | 54.0 | 54.0 | 54.0 |
| Copolymer of Example 58 | 4.0 | 3.0 | 4.0 | 3.0 |
| Perfume B | 0.05 | 0.2 | 0.1 | 0.15 |

These products are prepared by first dissolving the polymer in the ethanol with stirring. The water and fragrance are then added with stirring. The resulting hair spray compositions can then be packaged in a nonaerosol spray pump. Alternatively, the compositions can be combined with conventional propellants and packaged in an aerosol spray.

These hair sprays are useful for application to the hair to provide a styling and holding benefit.

Examples 63–65
Mousse

Mousse compositions are prepared from the following components utilizing conventional mixing techniques.

| Ingredients | 63 | 64 | 65 |
| --- | --- | --- | --- |
| Water | QS 100 | QS 100 | QS 100 |
| Copolymer of Example 58 | 3.00 | 2.50 | 3.50 |
| Lauramide DEA | 0.33 | 0.33 | 0.33 |
| Sodium Methyl Oleyl Taurate | 1.67 | 1.67 | 1.67 |
| DMDM Hydantoin | 0.78 | 0.78 | 0.78 |
| Disodium EDTA | 0.20 | 0.20 | 0.20 |
| Polyoxyalkylated isostearyl alcohol[(1)] | 0.10 | 0.10 | 0.10 |
| Perfume B | 0.10 | 0.10 | 0.10 |
| Propellant[(2)] | 7.0 | 7.0 | 7.0 |

[(2)]Available as Aerosurf ® 66-E10.
[(3)]Available as a mixture of about 82.46% isobutane, about 16.57% propane, and about 0.001% butane.

These products are prepared by first dissolving the polymer in water with stirring. The remaining ingredients, except the propellant, are then added with stirring. The resulting mousse concentrate can then be combined with conventional propellants (e.g., Propellant A46) and packaged in an aerosol spray. These mousses are useful for application to the hair to provide a styling and holding benefit.

Examples 66–68
Hair Tonic

Hair tonic compositions are prepared from the following components utilizing conventional mixing techniques.

| Ingredients | 66 | 67 | 68 |
| --- | --- | --- | --- |
| Ethanol | QS 100 | QS 100 | QS 100 |
| Copolymer of Example 58 | 0.75 | 1.00 | 1.25 |
| Perfume A | 0.10 | — | — |
| Perfume A | — | 0.20 | 0.30 |

These products are prepared by dissolving the polymer in the ethanol with stirring and then adding the fragrance and any colors.

These hair tonics are useful for application to the hair to provide a styling and holding benefit.

Example 69
Hair Conditioner

A hair conditioner composition is prepared from the following components utilizing conventional mixing techniques.

| Ingredients | Weight % |
| --- | --- |
| Styling Agent Premix | |
| Copolymer of Example 58 | 1.00 |
| Silicone Premix | |
| Silicone gum, GE SE76[(1)] | 0.30 |
| Octamethyl cyclotetrasiloxane | 1.70 |
| Main Mix | |
| Water | QS 100 |
| Cetyl Alcohol | 1.00 |
| Quaternium 18[(2)] | 0.85 |
| Stearyl Alcohol | 0.70 |
| Hydroxethyl cellulose | 0.50 |
| Ceteareth-20 | 0.35 |
| Perfume A | 0.20 |
| Dimethicone copolyol | 0.20 |
| Citric Acid | 0.13 |
| Methylchloroisothiazolinone (and) methylisothiazolinone | 0.04 |
| Sodium Chloride | 0.01 |

[1]Commercially available from General Electric.
[2]Dimethyl Di(Hydrogenated Tallow) Ammonium Chloride The product is prepared by co-mixing all the Main Mix ingredients, heating to about 60° C. with mixing, and colloid milling while cooling to about 45° C. At this temperature, the two premixes are add separately with moderate agitation and the resultant conditioner is allowed to cool to room temperature.

This product is useful as a rinse off hair conditioner.

Example 70
Anti-Acne Composition

An anti-acne composition is made by combining the following components using conventional mixing technology.

| Ingredient | Weight % |
| --- | --- |
| Water | QS 100 |
| Salicylic Acid | 2.0 |
| Copolymer from Example 58[1] | 2.0 |
| Ethanol (SDA 40) | 40.0 |
| Perfume B | 0.05 |

The compositon display skin penetration of the salicylic acid as well as improved skin reel and residue characteristics and is useful for the treatment of acne.

Example 71
Topical Analgesic Composition

A topical analgesic composition is made by combining the following ingredients utilizing conventional mixing techniques.

| Ingredients | Weight % |
| --- | --- |
| Water, Purified | QS 100 |
| Ibuprofen | 2.0 |
| Copolymer from Example 58[1] | 2.0 |
| Ethanol (SDA 40) | 20.0 |
| Perfume B | 0.03 |

The compositions display skin penetration of the ibuprofen active as well as improved skin feel and residue characteristics together with excellent moisturizing, emolliency, rub-in and absorption characteristics.

Example 72
Sunless Tanning Composition

A composition for sunless tanning is made by combining the following ingredients utilizing conventional mixing techniques.

| Ingredients | Weight % |
|---|---|
| Phase A | |
| Water | qs 100 |
| Copolymer from Example 58 | 2.00 |
| Carbomer 934[1] | 0.20 |
| Carbomer 980[2] | 0.15 |
| Acrylic Acid Copolymer[3] | 0.15 |
| Phase B | |
| PPG-20 Methyl Glucose Ether Distearate | 2.00 |
| Tocopheryl Acetate | 1.20 |
| Mineral Oil | 2.00 |
| Stearyl Alcohol | 1.00 |
| Shea Butter | 1.00 |
| Cetyl Alcohol | 1.00 |
| Ceteareth-20 | 2.50 |
| Ceteth-2 | 1.00 |
| Ceteth-10 | 1.00 |
| Phase C | |
| DEA-Cetyl Phosphate | 0.75 |
| Phase D | |
| Dihydroxyacetone | 3.00 |
| Phase E | |
| Butylene Glycol | 2.00 |
| DMDM Hydantoin (and) Iodopropynyl Butylcarbamate | 0.25 |
| Phase F | |
| Perfume B | 1.00 |
| Cyclomethicone | 2.00 |

[1]Available as Carbopol ® 934 from B. F. Goodrich.
[2]Available as Carbopol ® 980 from B. F. Goodrich.
[3]Available as Pemulen ® TR1 from B. F. Goodrich.

In a suitable vessel the Phase A ingredients are dispersed in the water and heated to about 75°–85° C. In a separate vessel the Phase B ingredients are combined and heated to about 85°–90° C. until melted. Next, the DEA-Cetyl Phosphate is added to the liquid Phase B and stirred until dissolved. This mixture is then added to Phase A to form the emulsion. The emulsion is cooled to about 40°–45° C. with continued mixing. Next, in a separate vessel, the dihydroxyacetone is dissolved in water and the resulting solution is mixed into the emulsion. In another vessel, the Phase E ingredients are heated with mixing to about 40°–45° C. until a clear solution is formed and this solution is then added to the emulsion. Finally, the Phase F ingredients are added to the emulsion with mixing, which is then cooled to about 30°–35° C., and then to room temperature.

This emulsion is useful for topical application to the skin to provide an artificial tan.

Example 73

Sunscreen Composition

An oil-in-water emulsion is prepared by combining the following components utilizing conventional mixing techniques.

| Ingredients | Weight % |
|---|---|
| Phase A | |
| Water | QS 100 |
| Carbomer 954[1] | 0.24 |
| Carbomer 1342[2] | 0.16 |
| Copolymer from Example VI[3] | 1.75 |
| Disodium EDTA | 0.05 |
| Phase B | |
| Isoarachidyl Neopentanoate[4] | 2.00 |
| PVP Eicosene Copolymer[5] | 2.00 |
| Octyl Methoxycinnamate | 7.50 |
| Octocrylene | 4.00 |
| Oxybenzone | 1.00 |
| Titanium Dioxide | 2.00 |
| Cetyl Palmitate | 0.75 |
| Stearoxytrimethylsilane (and) Stearyl Alcohol[6] | 0.50 |
| Glyceryl Tribehenate[7] | 0.75 |
| Dimethicone | 1.00 |
| Tocopheryl Acetate | 0.10 |
| DEA-Cetyl Phosphate | 0.20 |
| Phase C | |
| Water | 2.00 |
| Triethanolamine 99% | 0.60 |
| Phase D | |
| Water | 2.00 |
| Perfume B | 0.05 |
| Butylene Glycol | 2.00 |
| DMDM Hydantoin (and) Iodopropynyl Butylcarbamate[8] | 0.25 |
| dL Panthenol | 1.00 |
| Phase E | |
| Cyclomethicone | 1.00 |

[1]Available as Carbopol® 954 from B. F. Goodrich.
[2]Available as Carbopol® 1342 from B. F. Goodrich.
[3]Alternatively, the sunscreen compositions are prepared using the copolymers of Examples VIII and IX.
[4]Available as Elefac I-205 from Bernel Chemical.
[5]Available as Ganex V-220 from GAF Corporation.
[6]Available as DC 580 Wax from Dow Corning.
[7]Available as Synchrowax HRC from Croda.
[8]Available as Glydant Plus from Lonza.

In a suitable vessel the Phase A ingredients are dispersed in the water and heated to about 75°–85° C. In a separate vessel the Phase B ingredients (except DEA-Cetyl Phosphate) are combined and heated to about 85°–95° C. until melted. Next, the DEA-Cetyl Phosphate is added to the liquid Phase B and stirred until dissolved. This mixture is then added to Phase A to form the emulsion. The Phase C ingredients are combined until dissolved and then added to the emulsion. The emulsion is then cooled to about 40°–45° C. with continued mixing. In another vessel, the Phase D ingredients are heated with mixing to about 40°–45° C. until a clear solution is formed and this solution is then added to the emulsion. Finally, the emulsion is cooled to about 35° C. and the Phase E ingredient is added and mixed.

This emulsion is useful for topical application to the skin to provide protection from the harmful effects of ultraviolent radiation.

Example 74

Facial Moisturizer

A leave-on facial emulsion composition containing a cationic hydrophobic surfactant is prepared by combining the following components utilizing conventional mixing techniques.

| Ingredients | Weight % |
| --- | --- |
| Water | QS 100 |
| Copolymer from Example 58 | 1.00 |
| Glycerin | 3.00 |
| Cetyl Palmitate | 3.00 |
| Cetyl Alcohol | 1.26 |
| Quaternium-22 | 1.00 |
| Glyceryl Monohydroxy Stearate | 0.74 |
| Dimethicone | 0.60 |
| Stearic Acid | 0.55 |
| Octyldodecyl Myristate | 0.20 |
| Perfume B | 0.06 |
| Carbomer 1342 | 0.125 |
| Tetrasodium EDTA | 0.10 |
| DMDM Hydantoin and Iodopropynyl Butyl Carbamate | 0.10 |
| Carbomer 951 | 0.075 |

This emulsion is useful for application to the skin as a moisturizer.

Examples 75–82

The following compositions are representative of antiperspirant composions herein.

| Ingredients | 75 | 76 | 77 | 78 | 79 | 80 | 81 | 82 |
| --- | --- | --- | --- | --- | --- | --- | --- | --- |
| N-Lauroyl-L-glutamic acid-di-n-butyl amide[1] | 4 | 5 | 1 | 3 | 2 | 2 | 2 | 1 |
| 12-hydroxystearic acid | 2 | 5 | 5 | 6 | 7 | 3 | 6 | 12 |
| Cyclomethicone D-5[2] | — | 40 | 49 | 39 | 43 | 40 | 43 | 46 |
| Polyphenylmethylsiloxane[3] | — | — | — | 3 | — | — | 5 | — |
| Light mineral oil[4] | 23 | — | — | — | — | — | — | — |
| Panalane-L-14E[5] | — | 15 | 10 | 11 | — | — | — | — |
| Isopropyl Myristate | — | 15 | 15 | 16 | — | — | 11 | — |
| Isopropyl Alcohol | — | — | — | — | 18 | — | — | — |
| Captex 200[6] | — | — | — | — | — | 15 | — | — |
| C12–C15 Alcohols Benzoate[7] | — | — | — | — | — | — | 8 | — |
| PPG-3 Myristyl Ether | — | — | — | — | — | — | — | 26 |
| Diisopropyl Sebacate[8] | 43 | — | — | — | — | — | — | — |
| Aluminum Zirconium Trichlorhydrex Gly[9] | 24.9 | 19.8 | 19.9 | 19.89 | — | 39.88 | 24.8 | — |
| Aluminum Chlorohydrate[10] | — | — | — | — | 29.86 | — | — | 9.85 |
| Perfume A | 0.1 | — | 0.01 | — | 0.14 | — | 0.2 | — |
| Perfume B | — | 0.02 | — | 0.11 | — | 0.12 | — | 0.15 |
| Talc | 3 | — | — | 2 | — | — | — | 5 |
|  | 100 | 100 | 100 | 100 | 100 | 100 | 100 | 100 |

[1]GP-1 supplied by Ajinomoto, Inc.
[2]Dow Corning 245 Fluid-cyclic polydimethylsiloxane
[3]Dow Corning 556 Fluid
[4]Benol White Mineral Oil supplied by Witco Chemical Corp.
[5]Polyisobutene supplied by Amoco Chemical Company
[6]Propylene glycol dicaprate/dicaprylate supplied by Capital City Products
[7]Finsolv ® TN supplied by Finetex
[8]Schercemol ® DIS supplied by Scher Chemicals Inc.
[9]Supplied by Westwood Chemical Co.
[10]Westchlor ® DM200 supplied by Westwood Chemical Co.

Example 83

The following is another example of a deodorant composition.

An antiperspirant stick composition of the present invention is prepared as follows. All of the ingredients described below are combined and heated to about 82° C. with agitation. The batch is then cooled to about 52° C. and poured into canisters.

| Ingredients | Weight % |
| --- | --- |
| Cyclomethicone D-5[1] | 39.8 |
| Light Mineral Oil[2] | 11.5 |
| Dimethicone (50 csk)[3] | 1.5 |
| Stearyl Alcohol | 14.0 |
| Hydrogenated Castor Oil[4] | 4.5 |
| Eicosanol | 0.2 |
| Talc | 1.4 |
| Fumed Silica[5] | 1.0 |
| Perfume A | 0.1 |
| Aluminum Chlorohydrate[6] | 26.0 |
|  | 100% |

[1]A 5 carbon cyclic polydimethylsiloxane supplied by G.E. Silicones
[2]Benol White Mineral Oil, supplied by Witco Chemical Corporation (viscosity = 18–20 csk at 40° C.; density = 0.839–0.855 g/cm$^3$)
[3]Supplied by Dow Corning
[4]Castor Wax MP 80, supplied by NL Industries
[5]Cab-O-Sil HS-5, supplied by Cabot Corporation
[6]Reheis 501 macrospherical aluminum chlorohydrate, supplied by Reheis Chemical Company

What is claimed is:

1. Personal treatment composition selected from the group consisting of: leave-on hair care composition and leave-on skin care composition, said personal treatment composition containing an effective amount, of from about 0.001% to about 50% by weight, of enduring perfume composition wherein said enduring perfume composition contains at least 70% of enduring perfume ingredients having a ClogP≧3.0 and a boiling point of ≧250° C. selected from the group consisting of: Allyl cyclohexane propionate; Ambrettolide; Amyl benzoate; Amyl-cinnamate; Amyl cinnamic aldehyde; Amyl cinnamic aldehyde dimethyl acetal; iso-Amyl salicylate; Aurantiol; Benzophenone; Benzyl salicylate; para-tert-Butyl cyclohexyl acetate; iso-Butyl quinoline; beta-Caryophyllene; Cadinene; Cedrol;

Cedryl acetate; Cedryl formate; Cinnamyl cinnamate; Cyclohexyl salicylate; Cyclamen aldehyde; Dibydro isojasmonate, Diphenyl methane; Diphenyl oxide; Dodecalactone; iso E super; Ethylene brassylate; Ethylmethyl phenyl glycidate, Ethyl undecylenate; Exaltolide; Galaxolide; Geranyl anthranilate; Geranyl phenyl acetate; Hexadecanolide; Hexenyl salicylate; Hexyl cinnamic aldehyde, Hexyl salicylate; alpha-Irone; Lilial (p-t-bucinal), Linalyl benzoate; 2-Methoxy naphthalene; Methyl dihydrojasmone; gamma-n-Methyl ionone; Musk indanone; Musk-ketone, Musk tibetine; Myristicin; Oxahexadecanolide-10; Oxahexadecanolide-11; Patchouli alcohol; Phantolide; Phenyl ethyl benzoate; Phenylethylphenylacetate; Phenyl heptanol; Phenyl hexanol; alpha-Santalol; Thibetolide; delta-Undecalactone; gamma-Undecalactone; Vetiveryl acetate; yara-yara; Ylangene; and mixtures thereof, said enduring perfume composition containing at least three different enduring perfume ingredients.

2. The composition of claim 1 wherein the hair care composition is selected from the group consisting of hair conditioner, hair spray, hair gel, hair tonic, mousse, hair curler and hair straightener.

3. The composition of claim 1 wherein the skin care composition is selected from the group consisting of deodorant, antiperspirant, skin lotion, skin moisturizer, skin softening lotion, suntan lotion, sun screen lotion, sunless tanning composition, skin bleaching composition, topical pharmaceutical skin care composition, perfume, and cologne.

4. The composition of claim 3 wherein the topical pharmaceutical skin care composition is selected from the group consisting of anti-acne composition, non-steroidal anti-flammatory composition, steroidal anti-flammatory composition, antipruritic composition, anesthetic composition, and antimicrobial composition.

5. The composition of claim 1 wherein the enduring perfume composition is at a level of from about 0.005% to about 6% by weight.

6. The composition of claim 5 wherein the enduring perfume composition is at a level of from about 0.01% to about 4% by weight.

7. The composition of claim 2 wherein the enduring perfume composition is at a level of from about 0.01% to about 1% by weight.

8. The composition of claim 1 wherein said enduring perfume composition has at least about 75% said enduring perfume ingredients.

9. The composition of claim 8 wherein said enduring perfume composition has at least about 80% said enduring perfume ingredients.

10. The composition of claim 9 wherein said enduring perfume composition has at least about 85% said enduring perfume ingredients.

11. The composition of claim 9 wherein the enduring perfume composition is at a level of from about 0.01% to about 4% by weight.

12. The process of using the composition of claim 1 comprising the step of applying an effective amount of said composition to at least one part of the human body.

* * * * *